United States Patent
Luo et al.

(10) Patent No.: US 9,957,518 B2
(45) Date of Patent: May 1, 2018

(54) METHODS AND COMPOSITIONS FOR MODULATING GENE EXPRESSION IN PLANTS

(71) Applicant: Clemson University, Anderson, SC (US)

(72) Inventors: Hong Luo, Clemson, SC (US); Ning Yuan, Clemson, SC (US)

(73) Assignee: Clemson University, Anderson, SC (US)

( * ) Notice: Subject to any disclaimer, the term of this patent is extended or adjusted under 35 U.S.C. 154(b) by 0 days. days.

(21) Appl. No.: 15/002,819

(22) Filed: Jan. 21, 2016

(65) Prior Publication Data

US 2016/0215295 A1    Jul. 28, 2016

Related U.S. Application Data

(60) Provisional application No. 62/106,298, filed on Jan. 22, 2015.

(51) Int. Cl.
*C12N 15/82* (2006.01)
*C07K 14/415* (2006.01)

(52) U.S. Cl.
CPC ........ *C12N 15/8222* (2013.01); *C07K 14/415* (2013.01); *C12N 15/8216* (2013.01); *C12N 15/8225* (2013.01)

(58) Field of Classification Search
None
See application file for complete search history.

(56) References Cited

U.S. PATENT DOCUMENTS

2012/0084885 A1* 4/2012 Alexandrov ....... C12N 15/8216
800/298

OTHER PUBLICATIONS

Pfister, K. "Functional Analysis of the Strubbelig-Receptor Family in *Arabidopsis thaliana*" (2008) Dissertation from Technische Universitat Munchen; pp. 1-99.*

Cai et al. A rice promoter containing both novel positive and negative cis-elements for regulation of green tissue-specific gene expression in transgenic plants. (2007) Plant Biotechnology Journal; vol. 5; pp. 664-674.*

Morales et al. Changes in the volatile composition of virgin olive oil during oxidation: flavors and off-flavors. (1997) J. Agric. Food Chem.; vol. 45; pp. 2666-2673.*

* cited by examiner

*Primary Examiner* — Cathy Kingdon Worley
(74) *Attorney, Agent, or Firm* — Myers Bigel, P.A.

(57) ABSTRACT

The present invention provides methods and compositions for regulation of gene expression in plants. In particular, the invention provides nucleic acids that can confer tissue specific and constitutive expression to operably linked polynucleotides of interest.

20 Claims, 13 Drawing Sheets

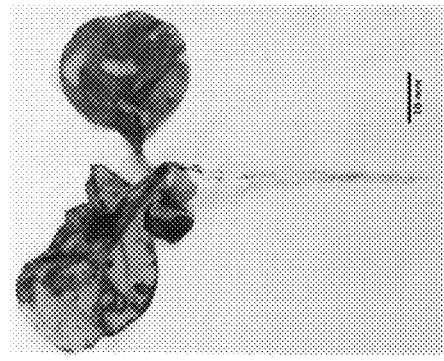
Fig. 8B
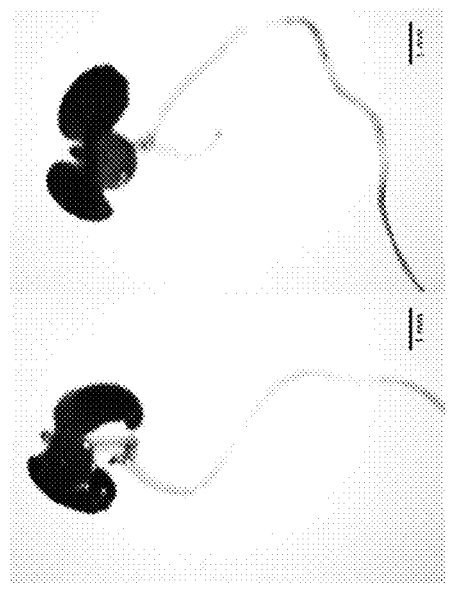
Fig. 8A
7 days old plants
3 weeks old plant
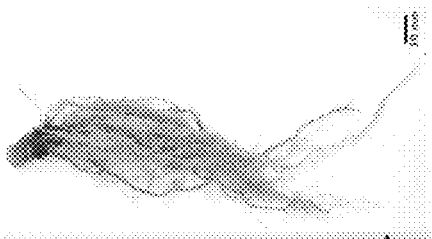
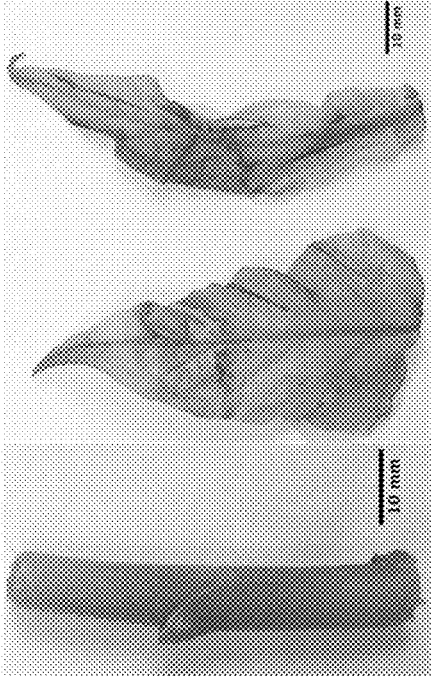
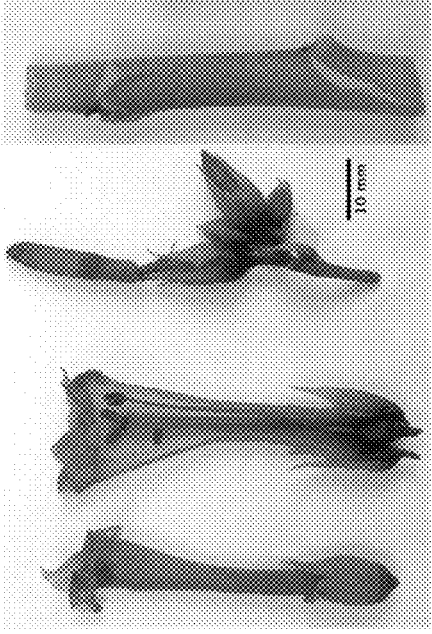
Fig. 8C
Flower · Stem · Leaf · Root
Florescent tobacco plant

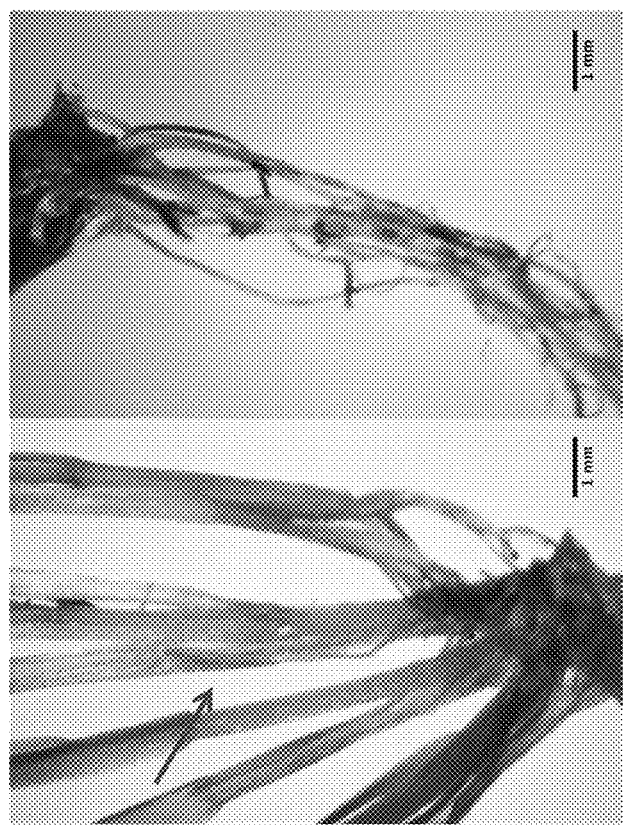
Fig. 9 Agrostis stolonifera (Creeping bentgrass)

SEQUENCE LISTING

<160> NUMBER OF SEQ ID NOS: 37

<210> SEQ ID NO 1
<211> LENGTH: 1524
<212> TYPE: DNA
<213> ORGANISM: Arabidopsis thaliana

<400> SEQUENCE: 1

```
ctcggtagag gtcctgatta tatttcctat tgtatcgcgt ggatcattat tttaccctat      60
atatccttta caactatcct aaattttgtg catcaatttt atttttttgta agcaatgaac     120 ttctaattac aatagaagtt caaagtcttt tttccccccat gtttcagttt attccaacta    180
accatgaatt aaataatggg tggtggtgca tgtttctttt accaaaaata accatgaatt     240
aataactata gcatttgctt atgacccttc aacttctaac atgcagagtg acctttgtat     300
ataagcagcg tcacctaaga gatccagtca ccagtacgga aacagaagaa attcctgaca    360
```

```
ataaaagaag caaactcacc tcctagcttt tcaaattaca aaattgatga aatttggttt     420
atagattctc ttcattgggg caaatcatag aaatagtttg gtcgacattg gggcaaaaca     480
tggaatagaa cgggacaatt ttggaaataa cagattgaga gcatcagcaa cggcaacttc     540
tcaacttccg attctcaata tatgtgtgaa cataaatata agtgtgaaca caaatattat     600
taatatttaa ttggaaagta ttttaattaa accaatgatt gaatgacaac tgtgagaaac     660
gttgtcgatg agtttttctt ggtttctcta agaaaacttt cccttacct ctctcctcct      720
tttgacattt ttttcttatt ttattggtga gagatttat gagaaactcc cgttggagtt      780
ggtctgagtg tccttcaaac attttaaaa taaatatcac acattcacac tataactgct      840
tattctactt ttaaaaccat aaaatgattg ctccaagcca ttgggaatat aatcaaatat     900
atatacttaa tccaaaaggt acataaaatt tggtgacaaa aatttacttt tgttggaaa      960
aagaaagtat ctgagcagaa tattggacgg agcaaagaaa caagagaagg atatcaagta   1020
gcacaacttg acaaattgac aaaggatcaa acaagattca tatgttgtaa taatctatag   1080
tcaactaagg caacacattg cttacaaact acaaagtgaa gtcattgtca ttaatggtta   1140
tcagatgatt acttatgtcc acataatata gaaaaagca tatccttgac aatattgaag    1200
ataagaaaat tcaaggagaa tctaaagact gattgttctt tcgagttgac ttagtcaacg   1260
gttttgtggt tccaacttgt aagctgtaat tacggctggg caaggtaacg gaccactctt   1320
gtcattttct ctcaaccaaa tcattttaca ccatcgaaat aatatcctca ttaaatgtgt   1380
tccctcaatt atttgattca ttaatgtgac acttataaga atttgactta ggactttgag   1440
aaatacctca tatacataat cataaactta tatgcatagc tttgctaact caaaaaaaa    1500
aacagatccc ttctttgcat agta                                           1524

<210> SEQ ID NO 2
<211> LENGTH: 1022
<212> TYPE: DNA
<213> ORGANISM: Arabidopsis thaliana

<400> SEQUENCE: 2
ggaaataaca gattgagagc atcagcaacg gcaacttctc aacttccgat tctcaatata     60
tgtgtgaaca taaatataag tgtgaacaca atattatta atatttaatt ggaaagtatt    120
ttaattaaac caatgattga atgacaactg tgagaaacgt tgtcgatgag ttttttcttgg   180
tttctctaaa gaaaactttc ccttacctct ctcctccttt tgacattttt ttcttatttt    240
attggtgaga gattttatga gaaactcccg ttggagttgg tctgagtgtc cttcaaacat    300
ttttaaaata aatatcacac attcacacta taactgctta ttctactttt aaaaccataa    360
aatgattgct ccaagccatt gggaatataa tcaaatatat acttaatc caaaaggtac      420
ataaaatttg gtgacaaaaa tttactttt gttggaaaaa gaaagtatct gagcagaata    480
ttggacggag caaagaaaca agagaaggat atcaagtagc acaacttgac aaattgacaa    540
aggatcaaac aagattcata tgttgtaata atctatagtc aactaaggca acacattgct    600
tacaaactac aaagtgaagt cattgtcatt aatggttatc agatgattac ttatgtccac    660
ataatataga aaaagcata tccttgacaa tattgagat aagaaaattc aaggagaatc     720
taaagactga ttgttctttc gagttgactt agtcaacggt tttgtggttc aacttgtaa    780
gctgtaatta cggctgggca aggtaacgga ccactcttgt cattttctct caaccaaatc    840
attttacacc atcgaaataa tatcctcatt aaatgtgttc cctcaattat ttgattcatt    900
aatgtgacac ttataagaat ttgacttagg actttgagaa atacctcata tacataatca    960
```

```
taaacttata tgcatagctt tgctaactca aaaaaaaaaa cagatcccct ctttgcatag   1020
ta                                                                 1022

<210> SEQ ID NO 3
<211> LENGTH: 383
<212> TYPE: DNA
<213> ORGANISM: Arabidopsis thaliana

<400> SEQUENCE: 3
cagatgatta cttatgtcca cataatatag aaaaaagcat atccttgaca atattgaaga     60
taagaaaatt caaggagaat ctaaagactg attgttcttt cgagttgact tagtcaacgg    120
ttttgtggtt ccaacttgta agctgtaatt acggctgggc aaggtaacgg accactcttg    180
tcattttctc tcaaccaaat cattttacac catcgaaata atatcctcat taaatgtgtt    240
ccctcaatta tttgattcat taatgtgaca cttataagaa tttgacttag gactttgaga    300
aatacctcat atacataatc ataaacttat atgcatagct tgctaactc aaaaaaaaaa     360 acagatccct tctttgcata gta                                           383

<210> SEQ ID NO 4
<211> LENGTH: 5
<212> TYPE: PRT
<213> ORGANISM: Artificial
<220> FEATURE:
<223> OTHER INFORMATION: poly-Arg tag

<400> SEQUENCE: 4

Arg Arg Arg Arg Arg
1               5

<210> SEQ ID NO 5
<211> LENGTH: 6
<212> TYPE: PRT
<213> ORGANISM: Artificial
<220> FEATURE:
<223> OTHER INFORMATION: poly-Arg tag

<400> SEQUENCE: 5

Arg Arg Arg Arg Arg Arg
1               5

<210> SEQ ID NO 6
<211> LENGTH: 6
<212> TYPE: PRT
<213> ORGANISM: Artificial
<220> FEATURE:
<223> OTHER INFORMATION: poly-His tag

<400> SEQUENCE: 6

His His His His His His
1               5

<210> SEQ ID NO 7
<211> LENGTH: 8
<212> TYPE: PRT
<213> ORGANISM: Artificial
<220> FEATURE:
<223> OTHER INFORMATION: FLAG tag

<400> SEQUENCE: 7

Asp Tyr Lys Asp Asp Asp Asp Lys
1               5
```

<210> SEQ ID NO 8
<211> LENGTH: 8
<212> TYPE: PRT
<213> ORGANISM: Artificial
<220> FEATURE:
<223> OTHER INFORMATION: Strep-tag II

<400> SEQUENCE: 8

Trp Ser His Pro Gln Phe Glu Lys
1               5

<210> SEQ ID NO 9
<211> LENGTH: 10
<212> TYPE: PRT
<213> ORGANISM: Artificial
<220> FEATURE:
<223> OTHER INFORMATION: c-myc tag

<400> SEQUENCE: 9

Glu Gln Lys Leu Ile Ser Glu Glu Asp Leu
1               5                   10

<210> SEQ ID NO 10
<211> LENGTH: 33
<212> TYPE: DNA
<213> ORGANISM: Artificial
<220> FEATURE:
<223> OTHER INFORMATION: PCR primer

<400> SEQUENCE: 10
acctaggctc ggtagaggtc ctgattatat ttc                           33

<210> SEQ ID NO 11
<211> LENGTH: 31
<212> TYPE: DNA
<213> ORGANISM: Artificial
<220> FEATURE:
<223> OTHER INFORMATION: PCR primer

<400> SEQUENCE: 11
actcgagtta ctatgcaaag aagggatctg t                             31

<210> SEQ ID NO 12
<211> LENGTH: 27
<212> TYPE: DNA
<213> ORGANISM: Artificial
<220> FEATURE:
<223> OTHER INFORMATION: PCR primer

<400> SEQUENCE: 12
acctagggga aataacagat tgagagc                                  27

<210> SEQ ID NO 13
<211> LENGTH: 28
<212> TYPE: DNA
<213> ORGANISM: Artificial
<220> FEATURE:
<223> OTHER INFORMATION: PCR primer

<400> SEQUENCE: 13
acctaggcag atgattactt atgtccac                                 28

<210> SEQ ID NO 14
<211> LENGTH: 502
<212> TYPE: DNA
<213> ORGANISM: Arabidopsis thaliana

<400> SEQUENCE: 14

```
ctcggtagag gtcctgatta tatttcctat tgtatcgcgt ggatcattat tttaccctat        60
atatccttta caactatcct aaattttgtg catcaatttt attttttgta agcaatgaac       120
ttctaattac aatagaagtt caaagtcttt tttcccccat gtttcagttt attccaacta       180
accatgaatt aaataatggg tggtggtgca tgtttctttt accaaaaata accatgaatt       240
aataactata gcatttgctt atgacccttc aacttctaac atgcagagtg acctttgtat       300
ataagcagcg tcacctaaga gatccagtca ccagtacgga aacagaagaa attcctgaca       360
ataaaagaag caaactcacc tcctagcttt tcaaattaca aaattgatga aatttggttt       420
atagattctc ttcattgggg caaatcatag aaatagtttg gtcgacattg gggcaaaaca       480
tggaatagaa cgggacaatt tt                                                502
```

<210> SEQ ID NO 15
<211> LENGTH: 660
<212> TYPE: DNA
<213> ORGANISM: Arabidopsis thaliana

<400> SEQUENCE: 15

```
ggaaataaca gattgagagc atcagcaacg gcaacttctc aacttccgat tctcaatata        60
tgtgtgaaca taaatataag tgtgaacaca aatattatta atatttaatt ggaaagtatt       120
ttaattaaac caatgattga atgacaactg tgagaaacgt tgtcgatgag ttttcttgg       180
tttctctaaa gaaacttttc ccttacctct ctcctccttt tgacattttt tcttatttt       240
attggtgaga gattttatga gaaactcccg ttggagttgg tctgagtgtc cttcaaacat       300
ttttaaaata aatatcacac attcacacta taactgctta ttctactttt aaaaccataa       360
aatgattgct ccaagccatt gggaatataa tcaaatatat atacttaatc caaaaggtac       420
ataaaatttg gtgacaaaaa tttactttt gttggaaaaa gaaagtatct gagcagaata       480
ttggacggag caaagaaaca agagaaggat atcaagtagc acaacttgac aaattgacaa       540
aggatcaaac aagattcata tgttgtaata atctatagtc aactaaggca acacattgct       600
tacaaactac aaagtgaagt cattgtcatt aatggttatc agatgattac ttatgtccac       660
```

<210> SEQ ID NO 16
<211> LENGTH: 1162
<212> TYPE: DNA
<213> ORGANISM: Arabidopsis thaliana

<400> SEQUENCE: 16

```
ctcggtagag gtcctgatta tatttcctat tgtatcgcgt ggatcattat tttaccctat        60
atatccttta caactatcct aaattttgtg catcaatttt attttttgta agcaatgaac       120
ttctaattac aatagaagtt caaagtcttt tttcccccat gtttcagttt attccaacta       180
accatgaatt aaataatggg tggtggtgca tgtttctttt accaaaaata accatgaatt       240
aataactata gcatttgctt atgacccttc aacttctaac atgcagagtg acctttgtat       300
ataagcagcg tcacctaaga gatccagtca ccagtacgga aacagaagaa attcctgaca       360
ataaaagaag caaactcacc tcctagcttt tcaaattaca aaattgatga aatttggttt       420
atagattctc ttcattgggg caaatcatag aaatagtttg gtcgacattg gggcaaaaca       480
tggaatagaa cgggacaatt ttggaaataa cagattgaga gcatcagcaa cggcaacttc       540
tcaacttccg attctcaata tatgtgtgaa cataaatata agtgtgaaca caaatattat       600
```

```
taatatttaa ttggaaagta ttttaattaa accaatgatt gaatgacaac tgtgagaaac      660
gttgtcgatg agttttttctt ggtttctcta agaaaacttt tcccttacct ctctcctcct     720
tttgacattt ttttcttatt ttattggtga gagattttat gagaaactcc cgttggagtt     780
ggtctgagtg tccttcaaac attttttaaaa taaatatcac acattcacac tataactgct    840
tattctactt ttaaaaccat aaaatgattg ctccaagcca ttgggaatat aatcaaatat      900
atatacttaa tccaaaaggt acataaaatt tggtgacaaa atttacttt ttgttggaaa      960 aagaaagtat ctgagcagaa tattggacgg agcaaagaaa caagagaagg atatcaagta   1020
gcacaacttg acaaattgac aaaggatcaa acaagattca tatgttgtaa taatctatag   1080
tcaactaagg caacacattg cttacaaact acaaagtgaa gtcattgtca ttaatggtta   1140
tcagatgatt acttatgtcc ac                                             1162

<210> SEQ ID NO 17
<211> LENGTH: 885
<212> TYPE: DNA
<213> ORGANISM: Artificial
<220> FEATURE:
<223> OTHER INFORMATION: Sfr3 b region deletion promoter construct
      sequence

<400> SEQUENCE: 17
ctcggtagag gtcctgatta tatttcctat tgtatcgcgt ggatcattat tttaccctat        60
atatccttta caactatcct aaattttgtg catcaatttt atttttgta agcaatgaac      120 ttctaattac aatagaagtt caaagtcttt tttcccccat gtttcagttt attccaacta     180
accatgaatt aaataatggg tggtggtgca tgtttctttt accaaaaata accatgaatt     240
aataactata gcatttgctt atgacccttc aacttctaac atgcagagtg accttttgtat   300 ataagcagcg tcacctaaga gatccagtca ccagtacgga aacagaagaa attcctgaca   360
ataaaagaag caaactcacc tcctagcttt tcaaattaca aaattgatga aatttggttt    420
atagattctc ttcattgggg caaatcatag aaatagtttg gtcgacattg gggcaaaaca   480
tggaatagaa cgggacaatt ttcagatgat tacttatgtc cacataatat agaaaaaagc    540
atatccttga caatattgaa gataagaaaa ttcaaggaga atctaaagac tgattgttct    600
ttcgagttga cttagtcaac ggttttgtgg ttccaacttg taagctgtaa ttacggctgg    660
gcaaggtaac ggaccactct tgtcattttc tctcaaccaa atcattttac accatcgaaa    720
taatatcctc attaaatgtg ttccctcaat tatttgattc attaatgtga cacttataag    780
aatttgactt aggactttga gaaataccctc atatacaaa tcataaactt atatgcatag    840
ctttgctaac tcaaaaaaaa aaacagatcc cttctttgca tagta                    885

<210> SEQ ID NO 18
<211> LENGTH: 680
<212> TYPE: DNA
<213> ORGANISM: Artificial
<220> FEATURE:
<223> OTHER INFORMATION: Sfr3 b region deletion promoter construct
      sequence

<400> SEQUENCE: 18
gaatagaacg ggacaatttt ggaaataaca gattgagagc atcagcaacg gcaacttctc       60
aacttccgat tctcaatata tgtgtgaaca taaatataag tgtgaacaca aatattatta     120
atatttaatt ggaaagtatt ttaattaaac caatgattga atgacaactg tgagaaacgt    180
tgtcgatgag ttttttcttgg tttctctaaa gaaaactttc ccttacctct ctcctccttt   240
```

```
tgacattttt ttcttatttt attggtgaga gattttatga gaaactcccg ttggagttgg    300
tctgagtgtc cttcaaacat ttttaaaata aatatcacac attcacacta taactgctta    360
ttctactttt aaaaccataa aatgattgct ccaagccatt gggaatataa tcaaatatat    420
atacttaatc caaaaggtac ataaaatttg gtgacaaaaa tttacttttt gttggaaaaa    480
gaaagtatct gagcagaata ttggacggag caaagaaaca agagaaggat atcaagtagc    540
acaacttgac aaattgacaa aggatcaaac aagattcata tgttgtaata atctatagtc    600
aactaaggca acacattgct tacaaactac aaagtgaagt cattgtcatt aatggttatc    660
agatgattac ttatgtccac                                                680
```

<210> SEQ ID NO 19
<211> LENGTH: 700
<212> TYPE: DNA
<213> ORGANISM: Artificial
<220> FEATURE:
<223> OTHER INFORMATION: Sfr3 b region deletion promoter construct
      sequence

<400> SEQUENCE: 19

```
cgacattggg gcaaaacatg gaatagaacg ggacaatttt ggaaataaca gattgagagc    60
atcagcaacg gcaacttctc aacttccgat tctcaatata tgtgtgaaca taaatataag    120
tgtgaacaca aatattatta atatttaatt ggaaagtatt ttaattaaac caatgattga    180
atgacaactg tgagaaacgt tgtcgatgag ttttcttgg tttctctaaa gaaaactttc     240
ccttacctct ctcctccttt tgacattttt ttcttatttt attggtgaga gattttatga    300
gaaactcccg ttggagttgg tctgagtgtc cttcaaacat ttttaaaata aatatcacac    360
attcacacta taactgctta ttctactttt aaaaccataa aatgattgct ccaagccatt    420
gggaatataa tcaaatatat atacttaatc caaaaggtac ataaaatttg gtgacaaaaa    480
tttacttttt gttggaaaaa gaaagtatct gagcagaata ttggacggag caaagaaaca    540
agagaaggat atcaagtagc acaacttgac aaattgacaa aggatcaaac aagattcata    600
tgttgtaata atctatagtc aactaaggca acacattgct tacaaactac aaagtgaagt    660
cattgtcatt aatggttatc agatgattac ttatgtccac                          700
```

<210> SEQ ID NO 20
<211> LENGTH: 720
<212> TYPE: DNA
<213> ORGANISM: Artificial
<220> FEATURE:
<223> OTHER INFORMATION: Sfr3 b region deletion promoter construct
      sequence

<400> SEQUENCE: 20

```
aatcatagaa atagtttggt cgacattggg gcaaaacatg gaatagaacg ggacaatttt    60
ggaaataaca gattgagagc atcagcaacg gcaacttctc aacttccgat tctcaatata    120
tgtgtgaaca taaatataag tgtgaacaca aatattatta atatttaatt ggaaagtatt    180
ttaattaaac caatgattga atgacaactg tgagaaacgt tgtcgatgag ttttcttgg    240 tttctctaaa gaaaactttc ccttacctct ctcctccttt tgacattttt ttcttatttt    300
attggtgaga gattttatga gaaactcccg ttggagttgg tctgagtgtc cttcaaacat    360
ttttaaaata aatatcacac attcacacta taactgctta ttctactttt aaaaccataa    420
aatgattgct ccaagccatt gggaatataa tcaaatatat atacttaatc caaaaggtac    480
```

```
ataaaatttg gtgacaaaaa tttactttttt gttggaaaaa gaaagtatct gagcagaata      540
ttggacggag caaagaaaca agagaaggat atcaagtagc acaacttgac aaattgacaa      600
aggatcaaac aagattcata tgttgtaata atctatagtc aactaaggca acacattgct      660
tacaaactac aaagtgaagt cattgtcatt aatggttatc agatgattac ttatgtccac      720
```

<210> SEQ ID NO 21
<211> LENGTH: 740
<212> TYPE: DNA
<213> ORGANISM: Artificial
<220> FEATURE:
<223> OTHER INFORMATION: Sfr3 b region deletion promoter construct sequence

<400> SEQUENCE: 21

```
agattctctt cattggggca aatcatagaa atagtttggt cgacattggg gcaaaacatg       60
gaatagaacg ggacaatttt ggaaataaca gattgagagc atcagcaacg gcaacttctc      120
aacttccgat tctcaatata tgtgtgaaca taaatataag tgtgaacaca atatattatta    180 atatttaatt ggaaagtatt ttaattaaac caatgattga atgacaactg tgagaaacgt      240
tgtcgatgag ttttcttgg tttctctaaa gaaaactttc ccttacctct ctcctccttt      300
tgacattttt ttcttatttt attggtgaga gattttatga gaaactcccg ttggagttgg    360
tctgagtgtc cttcaaacat ttttaaaata aatatcacac attcacacta taactgctta    420
ttctactttt aaaaccataa aatgattgct ccaagccatt gggaatataa tcaaatatat      480
atacttaatc caaaaggtac ataaaatttg gtgacaaaaa tttactttttt gttggaaaaa    540 gaaagtatct gagcagaata ttggacggag caaagaaaca agagaaggat atcaagtagc      600
acaacttgac aaattgacaa aggatcaaac aagattcata tgttgtaata atctatagtc    660
aactaaggca acacattgct tacaaactac aaagtgaagt cattgtcatt aatggttatc    720
agatgattac ttatgtccac                                                  740
```

<210> SEQ ID NO 22
<211> LENGTH: 760
<212> TYPE: DNA
<213> ORGANISM: Artificial
<220> FEATURE:
<223> OTHER INFORMATION: Sfr3 b region deletion promoter construct sequence

<400> SEQUENCE: 22

```
attgatgaaa tttggtttat agattctctt cattggggca aatcatagaa atagtttggt       60
cgacattggg gcaaaacatg gaatagaacg ggacaatttt ggaaataaca gattgagagc      120
atcagcaacg gcaacttctc aacttccgat tctcaatata tgtgtgaaca taaatataag    180
tgtgaacaca atatattatta atatttaatt ggaaagtatt ttaattaaac caatgattga    240
atgacaactg tgagaaacgt tgtcgatgag ttttcttgg tttctctaaa gaaaactttc    300
ccttacctct ctcctccttt tgacattttt ttcttatttt attggtgaga gattttatga    360
gaaactcccg ttggagttgg tctgagtgtc cttcaaacat ttttaaaata aatatcacac      420
attcacacta taactgctta ttctactttt aaaaccataa aatgattgct ccaagccatt      480
gggaatataa tcaaatatat atacttaatc caaaaggtac ataaaatttg gtgacaaaaa      540 tttactttttt gttggaaaaa gaaagtatct gagcagaata ttggacggag caaagaaaca    600
agagaaggat atcaagtagc acaacttgac aaattgacaa aggatcaaac aagattcata      660
tgttgtaata atctatagtc aactaaggca acacattgct tacaaactac aaagtgaagt    720
```

```
cattgtcatt aatggttatc agatgattac ttatgtccac                        760
```

<210> SEQ ID NO 23
<211> LENGTH: 780
<212> TYPE: DNA
<213> ORGANISM: Artificial
<220> FEATURE:
<223> OTHER INFORMATION: Sfr3 b region deletion promoter construct
      sequence

<400> SEQUENCE: 23

```
ctagcttttc aaattacaaa attgatgaaa tttggtttat agattctctt cattggggca    60
aatcatagaa atagtttggt cgacattggg gcaaaacatg aatagaacg ggacaatttt   120
ggaaataaca gattgagagc atcagcaacg gcaacttctc aacttccgat tctcaatata   180
tgtgtgaaca taaatataag tgtgaacaca aatattatta atatttaatt ggaaagtatt   240
ttaattaaac caatgattga atgacaactg tgagaaacgt tgtcgatgag ttttcttgg    300
tttctctaaa gaaaactttc ccttacctct ctcctccttt tgacattttt ttcttatttt   360
attggtgaga gattttatga gaaactcccg ttggagttgg tctgagtgtc cttcaaacat   420
ttttaaaata aatatcacac attcacacta taactgctta ttctactttt aaaaccataa   480
aatgattgct ccaagccatt gggaatataa tcaaatatat atacttaatc caaaaggtac   540
ataaaatttg gtgacaaaaa tttacttttt gttggaaaaa gaaagtatct gagcagaata   600
ttggacggag caaagaaaca agagaaggat atcaagtagc acaacttgac aaattgacaa   660
aggatcaaac aagattcata tgttgtaata atctatagtc aactaaggca acacattgct   720
tacaaactac aaagtgaagt cattgtcatt aatggttatc agatgattac ttatgtccac   780
```

<210> SEQ ID NO 24
<211> LENGTH: 800
<212> TYPE: DNA
<213> ORGANISM: Artificial
<220> FEATURE:
<223> OTHER INFORMATION: Sfr3 b region deletion promoter construct
      sequence

<400> SEQUENCE: 24

```
aaaagaagca aactcacctc ctagcttttc aaattacaaa attgatgaaa tttggtttat    60
agattctctt cattggggca aatcatagaa atagtttggt cgacattggg gcaaaacatg   120
gaatagaacg ggacaatttt ggaaataaca gattgagagc atcagcaacg gcaacttctc   180
aacttccgat tctcaatata tgtgtgaaca taaatataag tgtgaacaca aatattatta   240
atatttaatt ggaaagtatt ttaattaaac caatgattga atgacaactg tgagaaacgt   300
tgtcgatgag ttttcttgg tttctctaaa gaaaactttc ccttacctct ctcctccttt    360
tgacattttt ttcttatttt attggtgaga gattttatga gaaactcccg ttggagttgg   420
tctgagtgtc cttcaaacat ttttaaaata aatatcacac attcacacta taactgctta   480
ttctactttt aaaaccataa aatgattgct ccaagccatt gggaatataa tcaaatatat   540
atacttaatc caaaaggtac ataaaatttg gtgacaaaaa tttacttttt gttggaaaaa   600
gaaagtatct gagcagaata ttggacggag caaagaaaca agagaaggat atcaagtagc   660
acaacttgac aaattgacaa aggatcaaac aagattcata tgttgtaata atctatagtc   720
aactaaggca acacattgct tacaaactac aaagtgaagt cattgtcatt aatggttatc   780
agatgattac ttatgtccac                                              800
```

<210> SEQ ID NO 25
<211> LENGTH: 820
<212> TYPE: DNA
<213> ORGANISM: Artificial
<220> FEATURE:
<223> OTHER INFORMATION: Sfr3 b region deletion promoter construct
      sequence

<400> SEQUENCE: 25

```
cagaagaaat tcctgacaat aaaagaagca aactcacctc ctagcttttc aaattacaaa      60
attgatgaaa tttggtttat agattctctt cattggggca aatcatagaa atagtttggt     120
cgacattggg gcaaaacatg gaatagaacg ggacaatttt ggaaataaca gattgagagc     180
atcagcaacg gcaacttctc aacttccgat tctcaatata tgtgtgaaca taaatataag     240
tgtgaacaca aatattatta atatttaatt ggaaagtatt ttaattaaac caatgattga     300
atgacaactg tgagaaacgt tgtcgatgag ttttcttgg tttctctaaa gaaaacttc     360 ccttacctct ctcctccttt tgacattttt ttcttatttt attggtgaga gatttttatga     420 gaaactcccg ttggagttgg tctgagtgtc cttcaaacat ttttaaaata aatatcacac     480
attcacacta taactgctta ttctactttt aaaaccataa aatgattgct ccaagccatt     540
gggaatataa tcaaatatat atacttaatc caaaaggtac ataaaatttg gtgacaaaaa     600 tttactttt gttggaaaaa gaaagtatct gagcagaata ttggacggag caaagaaaca     660
agagaaggat atcaagtagc acaacttgac aaattgacaa aggatcaaac aagattcata     720
tgttgtaata atctatagtc aactaaggca acacattgct tacaaactac aaagtgaagt     780
cattgtcatt aatggttatc agatgattac ttatgtccac                           820
```

<210> SEQ ID NO 26
<211> LENGTH: 840
<212> TYPE: DNA
<213> ORGANISM: Artificial
<220> FEATURE:
<223> OTHER INFORMATION: Sfr3 b region deletion promoter construct
      sequence

<400> SEQUENCE: 26

```
tccagtcacc agtacggaaa cagaagaaat tcctgacaat aaaagaagca aactcacctc      60
ctagcttttc aaattacaaa attgatgaaa tttggtttat agattctctt cattggggca     120
aatcatagaa atagtttggt cgacattggg gcaaaacatg gaatagaacg ggacaatttt     180
ggaaataaca gattgagagc atcagcaacg gcaacttctc aacttccgat tctcaatata     240
tgtgtgaaca taaatataag tgtgaacaca aatattatta atatttaatt ggaaagtatt     300
ttaattaaac caatgattga atgacaactg tgagaaacgt tgtcgatgag ttttcttgg     360 tttctctaaa gaaaacttc ccttacctct ctcctccttt tgacattttt ttcttatttt     420
attggtgaga gatttttatga gaaactcccg ttggagttgg tctgagtgtc cttcaaacat     480
ttttaaaata aatatcacac attcacacta taactgctta ttctactttt aaaaccataa     540
aatgattgct ccaagccatt gggaatataa tcaaatatat atacttaatc caaaaggtac     600
ataaaatttg gtgacaaaaa tttactttt gttggaaaaa gaaagtatct gagcagaata     660
ttggacggag caaagaaaca agagaaggat atcaagtagc acaacttgac aaattgacaa     720
aggatcaaac aagattcata tgttgtaata atctatagtc aactaaggca acacattgct     780
tacaaactac aaagtgaagt cattgtcatt aatggttatc agatgattac ttatgtccac     840
```

<210> SEQ ID NO 27
<211> LENGTH: 860
<212> TYPE: DNA
<213> ORGANISM: Artificial
<220> FEATURE:
<223> OTHER INFORMATION: Sfr3 b region deletion promoter construct sequence

<400> SEQUENCE: 27

```
aagcagcgtc acctaagaga tccagtcacc agtacggaaa cagaagaaat tcctgacaat      60
aaaagaagca aactcacctc ctagcttttc aaattacaaa attgatgaaa tttggtttat     120
agattctctt cattggggca aatcatagaa atagtttggt cgacattggg gcaaaacatg     180
gaatagaacg ggacaatttt ggaaataaca gattgagagc atcagcaacg gcaacttctc     240
aacttccgat tctcaatata tgtgtgaaca taaatataag tgtgaacaca aatattatta     300
atatttaatt ggaaagtatt ttaattaaac caatgattga atgacaactg tgagaaacgt     360
tgtcgatgag tttttcttgg tttctctaaa gaaaactttc ccttacctct ctcctccttt     420
tgacattttt ttcttatttt attggtgaga gattttatga gaaactcccg ttggagttgg     480
tctgagtgtc cttcaaacat ttttaaaata aatatcacac attcacacta taactgctta     540
ttctactttt aaaaccataa aatgattgct ccaagccatt gggaatataa tcaaatatat     600
atacttaatc caaaggtac ataaaatttg gtgacaaaaa tttactttt gttggaaaaa      660
gaaagtatct gagcagaata ttggacggag caaagaaaca agagaaggat atcaagtagc     720
acaacttgac aaattgacaa aggatcaaac aagattcata tgttgtaata atctatagtc     780
aactaaggca acacattgct tacaaactac aaagtgaagt cattgtcatt aatggttatc     840
agatgattac ttatgtccac                                                860
```

<210> SEQ ID NO 28
<211> LENGTH: 880
<212> TYPE: DNA
<213> ORGANISM: Artificial
<220> FEATURE:
<223> OTHER INFORMATION: Sfr3 b region deletion promoter construct sequence

<400> SEQUENCE: 28

```
gcagagtgac ctttgtatat aagcagcgtc acctaagaga tccagtcacc agtacggaaa      60
cagaagaaat tcctgacaat aaaagaagca aactcacctc ctagcttttc aaattacaaa     120
attgatgaaa tttggtttat agattctctt cattggggca aatcatagaa atagtttggt     180
cgacattggg gcaaaacatg gaatagaacg ggacaatttt ggaaataaca gattgagagc     240
atcagcaacg gcaacttctc aacttccgat tctcaatata tgtgtgaaca taaatataag     300
tgtgaacaca aatattatta atatttaatt ggaaagtatt ttaattaaac caatgattga     360
atgacaactg tgagaaacgt tgtcgatgag tttttcttgg tttctctaaa gaaaactttc     420
ccttacctct ctcctccttt tgacattttt ttcttatttt attggtgaga gattttatga     480
gaaactcccg ttggagttgg tctgagtgtc cttcaaacat ttttaaaata aatatcacac     540
attcacacta taactgctta ttctactttt aaaaccataa aatgattgct ccaagccatt     600
gggaatataa tcaaatatat atacttaatc caaaggtac ataaaatttg gtgacaaaaa     660
tttactttt gttggaaaaa gaaagtatct gagcagaata ttggacggag caaagaaaca     720
agagaaggat atcaagtagc acaacttgac aaattgacaa aggatcaaac aagattcata     780
tgttgtaata atctatagtc aactaaggca acacattgct tacaaactac aaagtgaagt     840
```

```
cattgtcatt aatggttatc agatgattac ttatgtccac         880
```

<210> SEQ ID NO 29
<211> LENGTH: 900
<212> TYPE: DNA
<213> ORGANISM: Artificial
<220> FEATURE:
<223> OTHER INFORMATION: Sfr3 b region deletion promoter construct
      sequence

<400> SEQUENCE: 29

```
gacccttcaa cttctaacat gcagagtgac ctttgtatat aagcagcgtc acctaagaga     60
tccagtcacc agtacggaaa cagaagaaat tcctgacaat aaaagaagca aactcacctc    120
ctagcttttc aaattacaaa attgatgaaa tttggtttat agattctctt cattggggca    180
aatcatagaa atagtttggt cgacattggg gcaaaacatg gaatagaacg ggacaatttt    240
ggaaataaca gattgagagc atcagcaacg gcaacttctc aacttccgat tctcaatata    300
tgtgtgaaca taaatataag tgtgaacaca aatattatta atatttaatt ggaaagtatt    360
ttaattaaac caatgattga atgacaactg tgagaaacgt tgtcgatgag ttttcttgg     420 tttctctaaa gaaactttc ccttacctct ctcctccttt tgacatttt ttcttatttt      480 attggtgaga gattttatga gaaactcccg ttggagttgg tctgagtgtc cttcaaacat    540
ttttaaaata aatatcacac attcacacta taactgctta ttctactttt aaaaccataa    600
aatgattgct ccaagccatt gggaatataa tcaaatatat atacttaatc caaaaggtac    660
ataaaatttg gtgacaaaaa tttactttt gttggaaaaa gaaagtatct gagcagaata     720
ttggacggag caaagaaaca agagaaggat atcaagtagc acaacttgac aaattgacaa    780
aggatcaaac aagattcata tgttgtaata atctatagtc aactaaggca acacattgct    840
tacaaactac aaagtgaagt cattgtcatt aatggttatc agatgattac ttatgtccac    900
```

<210> SEQ ID NO 30
<211> LENGTH: 920
<212> TYPE: DNA
<213> ORGANISM: Artificial
<220> FEATURE:
<223> OTHER INFORMATION: Sfr3 b region deletion promoter construct
      sequence

<400> SEQUENCE: 30

```
taactatagc atttgcttat gacccttcaa cttctaacat gcagagtgac ctttgtatat     60
aagcagcgtc acctaagaga tccagtcacc agtacggaaa cagaagaaat tcctgacaat    120
aaaagaagca aactcacctc ctagcttttc aaattacaaa attgatgaaa tttggtttat    180
agattctctt cattggggca aatcatagaa atagtttggt cgacattggg gcaaaacatg    240
gaatagaacg ggacaatttt ggaaataaca gattgagagc atcagcaacg gcaacttctc    300
aacttccgat tctcaatata tgtgtgaaca taaatataag tgtgaacaca aatattatta    360
atatttaatt ggaaagtatt ttaattaaac caatgattga atgacaactg tgagaaacgt    420
tgtcgatgag ttttcttgg tttctctaaa gaaactttc ccttacctct ctcctccttt      480 tgacatttt ttcttatttt attggtgaga gattttatga gaaactcccg ttggagttgg    540
tctgagtgtc cttcaaacat ttttaaaata aatatcacac attcacacta taactgctta    600
ttctactttt aaaaccataa aatgattgct ccaagccatt gggaatataa tcaaatatat    660
atacttaatc caaaaggtac ataaaatttg gtgacaaaaa tttactttt gttggaaaaa    720 gaaagtatct gagcagaata ttggacggag caaagaaaca agagaaggat atcaagtagc    780
```

| acaacttgac aaattgacaa aggatcaaac aagattcata tgttgtaata atctatagtc | 840 |
| aactaaggca acacattgct acaaactac aaagtgaagt cattgtcatt aatggttatc | 900 |
| agatgattac ttatgtccac | 920 |

<210> SEQ ID NO 31
<211> LENGTH: 940
<212> TYPE: DNA
<213> ORGANISM: Artificial
<220> FEATURE:
<223> OTHER INFORMATION: Sfr3 b region deletion promoter construct sequence

<400> SEQUENCE: 31

| caaaataac catgaattaa taactatagc atttgcttat gacccttcaa cttctaacat | 60 |
| gcagagtgac ctttgtatat aagcagcgtc acctaagaga tccagtcacc agtacggaaa | 120 |
| cagaagaaat tcctgacaat aaaagaagca aactcacctc ctagcttttc aaattacaaa | 180 |
| attgatgaaa tttggtttat agattctctt cattggggca aatcatagaa atagtttggt | 240 |
| cgacattggg gcaaaacatg aatagaacg ggacaatttt ggaaataaca gattgagagc | 300 |
| atcagcaacg gcaacttctc aacttccgat tctcaatata tgtgtgaaca taaatataag | 360 |
| tgtgaacaca atattatta atatttaatt ggaaagtatt ttaattaaac caatgattga | 420 |
| atgcaactg tgagaaacgt tgtcgatgag ttttcttgg tttctctaaa gaaactttc | 480 |
| ccttacctct ctcctccttt tgacattttt ttcttatttt attggtgaga gattttatga | 540 |
| gaaactcccg ttggagttgg tctgagtgtc cttcaaacat ttttaaaata aatatcacac | 600 |
| attcacacta taactgctta ttctactttt aaaaccataa aatgattgct ccaagccatt | 660 |
| gggaatataa tcaaatatat atacttaatc caaaaggtac ataaaatttg gtgacaaaaa | 720 |
| tttacttttt gttggaaaaa gaaagtatct gagcagaata ttggacggag caaagaaaca | 780 |
| agagaaggat atcaagtagc acaacttgac aaattgacaa aggatcaaac aagattcata | 840 |
| tgttgtaata atctatagtc aactaaggca acacattgct acaaactac aaagtgaagt | 900 |
| cattgtcatt aatggttatc agatgattac ttatgtccac | 940 |

<210> SEQ ID NO 32
<211> LENGTH: 960
<212> TYPE: DNA
<213> ORGANISM: Artificial
<220> FEATURE:
<223> OTHER INFORMATION: Sfr3 b region deletion promoter construct sequence

<400> SEQUENCE: 32

| gtggtgcatg tttctttac caaaataac catgaattaa taactatagc atttgcttat | 60 |
| gacccttcaa cttctaacat gcagagtgac ctttgtatat aagcagcgtc acctaagaga | 120 |
| tccagtcacc agtacggaaa cagaagaaat tcctgacaat aaaagaagca aactcacctc | 180 |
| ctagcttttc aaattacaaa attgatgaaa tttggtttat agattctctt cattggggca | 240 |
| aatcatagaa atagtttggt cgacattggg gcaaaacatg aatagaacg ggacaatttt | 300 |
| ggaaataaca gattgagagc atcagcaacg gcaacttctc aacttccgat tctcaatata | 360 |
| tgtgtgaaca taaatataag tgtgaacaca atattatta atatttaatt ggaaagtatt | 420 |
| ttaattaaac caatgattga atgcaactg tgagaaacgt tgtcgatgag ttttcttgg | 480 |
| tttctctaaa gaaactttc ccttacctct ctcctccttt tgacattttt ttcttatttt | 540 |

```
attggtgaga gattttatga gaaactcccg ttggagttgg tctgagtgtc cttcaaacat    600
ttttaaaata aatatcacac attcacacta taactgctta ttctactttt aaaaccataa    660
aatgattgct ccaagccatt gggaatataa tcaaatatat atacttaatc caaaaggtac    720
ataaaatttg gtgacaaaaa tttactttt  gttggaaaaa gaaagtatct gagcagaata    780
ttggacggag caaagaaaca agagaaggat atcaagtagc acaacttgac aaattgacaa    840
aggatcaaac aagattcata tgttgtaata atctatagtc aactaaggca acacattgct    900
tacaaactac aaagtgaagt cattgtcatt aatggttatc agatgattac ttatgtccac    960
```

<210> SEQ ID NO 33
<211> LENGTH: 980
<212> TYPE: DNA
<213> ORGANISM: Artificial
<220> FEATURE:
<223> OTHER INFORMATION: Sfr3 b region deletion promoter construct
      sequence

<400> SEQUENCE: 33

```
catgaattaa ataatgggtg gtggtgcatg tttcttttac caaaaataac catgaattaa     60
taactatagc atttgcttat gacccttcaa cttctaacat gcagagtgac ctttgtatat    120
aagcagcgtc acctaagaga tccagtcacc agtacggaaa cagaagaaat tcctgacaat    180
aaaagaagca aactcacctc ctagcttttc aaattacaaa attgatgaaa tttggtttat    240
agattctctt cattggggca aatcatagaa atagtttggt cgacattggg gcaaaacatg    300
gaatagaacg ggacaatttt ggaaataaca gattgagagc atcagcaacg gcaacttctc    360
aacttccgat tctcaatata tgtgtgaaca taaatataag tgtgaacaca atattatta    420 atatttaatt ggaaagtatt ttaattaaac caatgattga atgacaactg tgagaaacgt    480
tgtcgatgag ttttttcttgg tttctctaaa gaaaactttc ccttacctct ctcctccttt    540
tgacattttt ttcttatttt attggtgaga gattttatga gaaactcccg ttggagttgg    600
tctgagtgtc cttcaaacat ttttaaaata aatatcacac attcacacta taactgctta    660
ttctactttt aaaaccataa aatgattgct ccaagccatt gggaatataa tcaaatatat    720
atacttaatc caaaaggtac ataaaatttg gtgacaaaaa tttactttt  gttggaaaaa    780 gaaagtatct gagcagaata ttggacggag caaagaaaca agagaaggat atcaagtagc    840
acaacttgac aaattgacaa aggatcaaac aagattcata tgttgtaata atctatagtc    900
aactaaggca acacattgct tacaaactac aaagtgaagt cattgtcatt aatggttatc    960
agatgattac ttatgtccac                                                980
```

<210> SEQ ID NO 34
<211> LENGTH: 1000
<212> TYPE: DNA
<213> ORGANISM: Artificial
<220> FEATURE:
<223> OTHER INFORMATION: Sfr3 b region deletion promoter construct
      sequence

<400> SEQUENCE: 34

```
ttcagtttat tccaactaac catgaattaa ataatgggtg gtggtgcatg tttcttttac     60
caaaaataac catgaattaa taactatagc atttgcttat gacccttcaa cttctaacat    120
gcagagtgac ctttgtatat aagcagcgtc acctaagaga tccagtcacc agtacggaaa    180
cagaagaaat tcctgacaat aaaagaagca aactcacctc ctagcttttc aaattacaaa    240
attgatgaaa tttggtttat agattctctt cattggggca aatcatagaa atagtttggt    300
```

```
cgacattggg gcaaaacatg gaatagaacg ggacaatttt ggaaataaca gattgagagc      360
atcagcaacg gcaacttctc aacttccgat tctcaatata tgtgtgaaca taaatataag      420
tgtgaacaca aatattatta atatttaatt ggaaagtatt ttaattaaac caatgattga      480
atgacaactg tgagaaacgt tgtcgatgag ttttcttgg tttctctaaa gaaactttc        540 ccttacctct ctcctccttt tgacatttt ttcttatttt attggtgaga gattttatga       600
gaaactcccg ttggagttgg tctgagtgtc cttcaaacat ttttaaaata aatatcacac      660
attcacacta taactgctta ttctactttt aaaaccataa aatgattgct ccaagccatt      720
gggaatataa tcaaatatat atacttaatc caaaaggtac ataaaatttg gtgacaaaaa      780
tttacttttt gttggaaaaa gaaagtatct gagcagaata ttggacggag caaagaaaca      840
agagaaggat atcaagtagc acaacttgac aaattgacaa aggatcaaac aagattcata      900
tgttgtaata atctatagtc aactaaggca acacattgct tacaaactac aaagtgaagt      960
cattgtcatt aatggttatc agatgattac ttatgtccac                           1000
```

<210> SEQ ID NO 35
<211> LENGTH: 1020
<212> TYPE: DNA
<213> ORGANISM: Artificial
<220> FEATURE:
<223> OTHER INFORMATION: Sfr3 b region deletion promoter construct
      sequence

<400> SEQUENCE: 35

```
aagtctttt tccccccatgt ttcagtttat tccaactaac catgaattaa ataatgggtg       60
gtggtgcatg tttctttac caaaaataac catgaattaa taactatagc atttgcttat      120
gacccttcaa cttctaacat gcagagtgac ctttgtatat aagcagcgtc acctaagaga      180
tccagtcacc agtacggaaa cagaagaaat tcctgacaat aaaagaagca aactcacctc      240
ctagcttttc aaattacaaa attgatgaaa tttggtttat agattctctt cattggggca      300
aatcatagaa atagtttggt cgacattggg gcaaaacatg aatagaacg ggacaatttt       360 ggaaataaca gattgagagc atcagcaacg gcaacttctc aacttccgat tctcaatata      420
tgtgtgaaca taaatataag tgtgaacaca aatattatta atatttaatt ggaaagtatt      480
ttaattaaac caatgattga atgacaactg tgagaaacgt tgtcgatgag ttttcttgg      540 tttctctaaa gaaactttc ccttacctct ctcctccttt tgacattttt ttcttatttt      600
attggtgaga gattttatga gaaactcccg ttggagttgg tctgagtgtc cttcaaacat      660
ttttaaaata aatatcacac attcacacta taactgctta ttctactttt aaaaccataa      720
aatgattgct ccaagccatt gggaatataa tcaaatatat atacttaatc caaaaggtac      780
ataaaatttg gtgacaaaaa tttacttttt gttggaaaaa gaaagtatct gagcagaata      840
ttggacggag caaagaaaca agagaaggat atcaagtagc acaacttgac aaattgacaa      900
aggatcaaac aagattcata tgttgtaata atctatagtc aactaaggca acacattgct      960
tacaaactac aaagtgaagt cattgtcatt aatggttatc agatgattac ttatgtccac     1020
```

<210> SEQ ID NO 36
<211> LENGTH: 1040
<212> TYPE: DNA
<213> ORGANISM: Artificial
<220> FEATURE:
<223> OTHER INFORMATION: Sfr3 b region deletion promoter construct
      sequence

<400> SEQUENCE: 36

```
ctaattacaa tagaagttca aagtcttttt tcccccatgt ttcagtttat tccaactaac        60
catgaattaa ataatgggtg gtggtgcatg tttcttttac caaaaataac catgaattaa       120
taactatagc atttgcttat gacccttcaa cttctaacat gcagagtgac ctttgtatat       180
aagcagcgtc acctaagaga tccagtcacc agtacggaaa cagaagaaat tcctgacaat       240
aaaagaagca aactcacctc ctagcttttc aaattacaaa attgatgaaa tttggtttat       300
agattctctt cattggggca aatcatagaa atagtttggt cgacattggg gcaaaacatg       360
gaatagaacg ggacaatttt ggaaataaca gattgagagc atcagcaacg gcaacttctc       420
aacttccgat tctcaatata tgtgtgaaca taaatataag tgtgaacaca atattatta        480
atatttaatt ggaaagtatt ttaattaaac caatgattga atgacaactg tgagaaacgt       540
tgtcgatgag ttttcttgg tttctctaaa gaaaactttc ccttacctct ctcctccttt        600
tgacattttt ttcttatttt attggtgaga gatttttatga gaaactcccg ttggagttgg      660
tctgagtgtc cttcaaacat ttttaaaata aatatcacac attcacacta taactgctta      720
ttctactttt aaaaccataa aatgattgct ccaagccatt gggaatataa tcaaatatat       780
atacttaatc caaaggtac ataaaatttg gtgacaaaaa tttactttt gttggaaaaa         840
gaaagtatct gagcagaata ttggacggag caaagaaaca agagaaggat atcaagtagc       900
acaacttgac aaattgacaa aggatcaaac aagattcata tgttgtaata atctatagtc       960
aactaaggca acacattgct tacaaactac aaagtgaagt cattgtcatt aatggttatc      1020
agatgattac ttatgtccac                                                  1040
```

<210> SEQ ID NO 37
<211> LENGTH: 1060
<212> TYPE: DNA
<213> ORGANISM: Artificial
<220> FEATURE:
<223> OTHER INFORMATION: Sfr3 b region deletion promoter construct
sequence

<400> SEQUENCE: 37

```
tttttgtaag caatgaactt ctaattacaa tagaagttca aagtcttttt tcccccatgt        60
ttcagtttat tccaactaac catgaattaa ataatgggtg gtggtgcatg tttcttttac       120
caaaaataac catgaattaa taactatagc atttgcttat gacccttcaa cttctaacat       180
gcagagtgac ctttgtatat aagcagcgtc acctaagaga tccagtcacc agtacggaaa      240
cagaagaaat tcctgacaat aaaagaagca aactcacctc ctagcttttc aaattacaaa       300
attgatgaaa tttggtttat agattctctt cattggggca aatcatagaa atagtttggt       360
cgacattggg gcaaaacatg gaatagaacg ggacaatttt ggaaataaca gattgagagc      420
atcagcaacg gcaacttctc aacttccgat tctcaatata tgtgtgaaca taaatataag      480
tgtgaacaca atattatta atatttaatt ggaaagtatt ttaattaaac caatgattga       540
atgacaactg tgagaaacgt tgtcgatgag ttttcttgg tttctctaaa gaaaactttc       600
ccttacctct ctcctccttt tgacattttt ttcttatttt attggtgaga gatttttatga     660
gaaactcccg ttggagttgg tctgagtgtc cttcaaacat ttttaaaata aatatcacac      720
attcacacta taactgctta ttctactttt aaaaccataa aatgattgct ccaagccatt       780
gggaatataa tcaaatatat atacttaatc caaaggtac ataaaatttg gtgacaaaaa        840
tttactttt gttggaaaaa gaaagtatct gagcagaata ttggacggag caaagaaaca       900
```

```
agagaaggat atcaagtagc acaacttgac aaattgacaa aggatcaaac aagattcata    960
tgttgtaata atctatagtc aactaaggca acacattgct tacaaactac aaagtgaagt   1020
cattgtcatt aatggttatc agatgattac ttatgtccac                        1060
```

METHODS AND COMPOSITIONS FOR MODULATING GENE EXPRESSION IN PLANTS

STATEMENT OF PRIORITY

This application claims the benefit, under 35 U.S.C. § 119(e), of U.S. Provisional Application No. 62/106,298 was filed on Jan. 22, 2015, the entire contents of which is incorporated by reference herein.

STATEMENT OF GOVERNMENT SUPPORT

This invention was made with government support under grant number 2010-33522-21656, awarded by the United States Department of Agriculture—National Institute of Food and Agriculture. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 9662-63_ST25.txt, 36,708 bytes in size, generated on Jan. 20, 2016 and filed via EFS-Web, is provided in lieu of a paper copy. This Sequence Listing is hereby incorporated herein by reference into the specification for its disclosures.

FIELD OF INVENTION

The present invention relates to methods and compositions for regulation of gene expression in plants. In particular, the invention provides nucleic acids that can confer tissue specific and constitutive expression to operably linked nucleic acids.

BACKGROUND

A promoter is a specific DNA sequence that is involved in regulating the expression of operably linked downstream coding or other noncoding nucleic acids. In order to efficiently express a foreign gene in genetic modified organism (GMO), promoters exhibiting strong activity under various conditions and in different species have been identified.

Cauliflower mosaic virus (CaMV) 35S promoter is one of the most frequently used constitutive promoters in plant research (Odell et al. *Nature* 313(6005):810-812 (1985); Benfey, P. N. and N. H. Chua, *Science* 250(4983):959-966 (1990)). The CaMV 35S promoter, with a length of 343 base pairs, was isolated from a double-stranded cauliflower mosaic virus, in which the TATA box "tatataa" is localized between −32 bp to −26 bp. Another strong constitutive promoter was isolated from the maize Ubi-1 gene. The maize ubiquitin promoter exhibits very strong activity in most monocot tissues and so it is frequently utilized to drive foreign genes and expression cassettes in monocot plants (Cornejo et al. *Plant Mol Biol.* 23(3):567-81 (1993): Rooke et al. *Annals of Applied Biology* 136(2): 167-172 (2000): Castillo et al. *Bio-Technology* 12(13):1366-1371 (1994); Miki et al. *Plant Physiology* 138(4):1903-13 (2005)). Besides the CaMV 35S and maize ubiquitin promoters, other constitutive promoters used in transgenic plants include NOS and OCS, which were isolated from Ti plasmid of *Agrobacterium tumefaciens*. Both of these promoters have strong activity in dicots (Ebert et al. *Proc Natl Acad Sci USA* 84(16):5745-9 (1987); Velten et al. *EMBO J.* 3(12):2723-30 (1984); De Block et al. *The EMBO Journal*, 3(8):1681 (1984).). A further monocot promoter is that cloned from the rice actin 1 gene (McElroy et al. *The Plant Cell Online* 2(2):163-171 (1990)).

However, strong constitutive promoters such as those discussed above can have drawbacks. In some instances, accumulation of heterologous proteins or final metabolites may interrupt the metabolic homeostasis of a transgenic plant, which may result in repressed growth and development, or may even cause death. Furthermore, excess transcripts can result in repression of expression, or 'transgene silencing' or 'co-suppression' of the transgene (Dietz-Pfeilstetter, A., *Plant Science*, 179(3): 164-167 (2010); Kooter et al. *Trends Plant Sci.* 4(9):340-347(1999): Kumpatla et al. *Trends Plant Sci.* 3(3):97-104 (1998)). To avoid the adverse consequences brought by constitutive promoters in transgenic plants, inducible promoters and tissue specific promoters may be used, such as the light inducible rice original promoter rbcS, which is expressed in leaf and stem, the heat-inducible promoter Gmhsp17 cloned from soybean, the light inducible and green-tissue specific rice promoter Cab1R, the root and seedling specific Pyk10 promoter cloned from *Arabidopsis*, the fruit specific promoter E-8 cloned from tomato (*Lycopersicon esculentum*), and the seed specific promoter from the napin gene cloned from *Brassica napus* (Nomura, M., et al. *Plant Mol Biol.* 44(1):99-106 (2000); Schoffl, F., et al., *Mol Gen Genet.* 217(2-3):246-53 (1989); Luan, S. and L. Bogorad *Plant Cell* 4(8): p. 971-81 (1992); Ellerstrom, M., et al. *Plant Mol Biol.* 32(6): 1019-27 (1996); Krasnyanski, S. F., et al. *In Vitro Cellular & Developmental Biology—Plant* 37(4):427-433 (2001); Nitz, I., et al. *Plant Science,* 161(2):337-346 (2001)). However, a disadvantage of most inducible and tissue specific promoters is that their activities are generally weaker than that of constitutive promoters.

The present invention overcomes previous shortcomings in the art by providing tissue specific promoters useful for modulating gene expression in plants.

SUMMARY OF THE INVENTION

In one aspect, the present invention provides a recombinant nucleic acid molecule comprising: (a) a nucleotide sequence of any one of SEQ ID NOs:1-3, or SEQ ID NOs:14-17; (b) a nucleotide sequence having at least 70% identity to any one of the nucleotide sequences of (a); (c) a functional fragment of a nucleotide sequence of any one of (a) to (b); any combination of (a) to (c), above, wherein the nucleotide sequence of (a) and/or (b) and/or the functional fragment of (c) is operably linked to at least one heterologous polynucleotide of interest.

In a further aspect, a recombinant nucleic acid molecule is provided comprising: (a) a nucleotide sequence of any one of SEQ ID NOs:18-37, or any combination thereof; (b) a nucleotide sequence having at least 70% identity to any one of the nucleotide sequences of (a); (c) a functional fragment of a nucleotide sequence of any one of (a) to (b); or any combination of (a) to (c), above, wherein the nucleotide sequence of (a) and/or (b) and/or the functional fragment of (c) is operably linked to a heterologous promoter. In some embodiments, the recombinant nucleic acid molecule of the invention can be operably linked to a heterologous polynucleotide of interest.

In some aspects, the invention provides a method of producing a plant and/or a plant part expressing at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:1-3, or SEQ ID NOs:14-17; (b) a nucleotide sequence having at least 70% identity to any one of the nucleotide sequences of (a); (c) a functional fragment of a nucleotide sequence of (a) or (b); or any combination of (a) to (c), above, wherein the nucleotide sequence of (a) and/or (b) and/or the functional fragment of (c) is operably linked to at least one heterologous polynucleotide, thereby producing a plant and/or plant part expressing the at least one heterologous polynucleotide of interest.

In a further aspect, the invention provides a method of producing a plant and/or a plant part expressing at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:18-37, (b) a nucleotide sequence having at least 70% identity to any one of the nucleotide sequences of (a); (c) a functional fragment of a nucleotide sequence of (a) or (b), or any combination of (a) to (c), above, wherein the nucleotide sequence of (a) and/or (b) and/or the functional fragment of (c) is operably linked to a heterologous promoter and at least one heterologous polynucleotide; thereby producing a plant and/or plant part expressing the at least one heterologous polynucleotide of interest.

In an additional aspect, the present invention provides a method of producing a plant and/or a plant part having tissue specific expression of at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:1-3, or SEQ ID NOs:14-17, (b) a nucleotide sequence having at least 70% identity to any one of the nucleotide sequences of (a), (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide, thereby producing a plant having tissue specific expression of the at least one heterologous polynucleotide of interest. In some embodiments, the at least one heterologous polynucleotide of interest is not expressed in the roots.

In some aspects, the present invention provides a method of producing a plant and/or a plant part having tissue specific expression of at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:18-37, (b) a nucleotide sequence having at least 70% identity to any one of the nucleotide sequences of (a), (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide, thereby producing a plant having tissue specific expression of at least one heterologous polynucleotide of interest.

Additionally provided are expression cassettes and vectors comprising the recombinant nucleic acids of the invention; plants, plant parts, plant cells comprising a recombinant nucleic acid of the invention, expression cassettes, vectors as well as crops comprising plants comprising the recombinant nucleic acids of the invention and products produced from the plants, plant parts, plant cells and crops. In some particular aspects, the invention provides seeds and progeny plants produced from the plants of the invention.

These and other aspects of the invention are set forth in more detail in the description of the invention below.

BRIEF DESCRIPTION OF THE DRAWINGS

FIG. 1A shows that AtSIF3 belongs to AtSIF3 gene cluster localized closely together on *Arabidopsis* chromosome 1. FIG. 1B shows the primary structure of *Arabidopsis* LRR-RLK AtSIF3. AtSIF3 is a classic Leucine-Rich-Repeat Receptor Like Protein Kinase with the length of 884 amino acid residues, which contains a N-terminal signal peptide (SP), an extracellular domain with 3 LRRs (ER), a transmembrane domain (TM), and a cytoplasmic protein kinase domain (PK). FIG. 1C shows the leaf specific expression of AtSIF3 in *Arabidopsis thaliana* plants. Actin was used as a reference gene.

FIG. 2A shows the structure of the promoter region of AtSIF3. The AtSIF3 promoter has a length of 1536 bp (base pairs) and is randomly divided to 3 regions, including region a (from −1536 bp to −1033 bp), region b (from −1033 bp to −395 bp), and region c (from −395 bp to −12 bp). The three regions are cloned separately. STOP indicates the stop codon of the upstream gene. ATG indicates the start codon of AtSIF3. FIG. 2B shows schematic diagrams of the reporter systems used for investigation of AtSIF3 promoter activity. The three promoter regions (a, b, and c) of AtSIF3 are fused in indicated combinations and were constructed in the upstream of the GUS gene. FIG. 2C shows schematic diagrams of the reporter systems used as controls. CaMV 35s promoter and maize Ubi-1 promoter were cloned and constructed in the upstream of the GUS gene. Bar gene which encodes phosphinothricin N-acetyltransferase was driven by the CaMV 35S and used as selection maker in all binary vectors. The digits following the promoter name indicate the length of the promoter region.

FIG. 4A shows histochemical GUS-staining of two weeks old control plants. a and b: leaf and root tissues of wild type plants. c and d: leaf and root tissues of 35s/GUS plants. e and f: leaf and root tissues of Ubi/GUS plants. FIG. 4B shows histochemical GUS-staining of two week old *Arabidopsis* seedlings transformed with a GUS reporter gene under control of the entire Sif3 promoter (Sif3abc) or portions thereof Sif3a, Sif3b, Sif3c, Sif3ab, Sif3ac, or Sif3bc. a, b: leaf and root tissues of sif3abc/GUS plants. c, d: leaf and root tissues of srf3a/GUS plants. e, f: leaf and root tissues of sif3b/GUS plants. g, h: leaf and root tissues of srf3c/GUS plants. i, j: leaf and root tissues of sif3ab/GUS plants. k, l: leaf and root tissues of srf3ac/GUS plants. m, n: leaf and root tissues of sif3bc/GUS plants. More than 3 plants of each construct were stained and one representative was exhibited. Scale bar: 1 mm. Pictures were taken under an optical microscope. 35s: CaMV 35S promoter. Ubi: maize ubiquitin promoter.

FIG. 5A shows histochemical GUS-staining of four weeks old control plants. Panels a-e show different tissues of wild type plants. Panels f-j show different tissues of 35s/GUS plants. Panels k and o show different tissues of Ubi/GUS plants. FIG. 5B shows histochemical GUS-staining of four week old *Arabidopsis* seedlings transformed with a GUS reporter gene under control of the entire Sif3 promoter (Sif3abc) or portions thereof Sif3a. Sif3a, Sif3b, Sif3c, Sif3ab, Sif3ac, or Sif3bc. Panels 1-5 show different tissues of sif3abc/GUS plants. Panels 6-10 show different tissues of srf3a/GUS plants. Panels 11-15 show different tissues of sif3b/GUS plants. Panels 16-20 show different tissues of sif3c/GUS plants. Panels 21-25 show different tissues of sif3ab/GUS plants. Panels 26-30 show different tissues of srf3ac/GUS plants. Panels 31-35 show different tissues of sif3bc/GUS plants. More than 3 plants of each construct were stained and one representative was exhibited. Scale bar: 1 mm. Pictures were taken under an optical microscope. 35s: CaMV 35S promoter. Ubi: maize ubiquitin promoter.

FIG. 6A shows expression in roots. For each transgenic *Arabidopsis* line, two independent events were used. FIG. 6B shows expression in leaves. FIG. 6C shows expression in stems. FIG. 6D shows expression in seeds. For FIGS. 6B-6D, for each *Arabidopsis* line, plant samples were harvested from pooled plant tissues taken from at least 7 independent events. Error bars were derived from the standard deviation of three biological replicates and three technical replicates. Asterisks indicate the significant differences between CaMV 35S and other promoters. P<0.05 was considered to be statistically significant and marked as *. P<0.01 was considered to be statistically highly significant and marked as **.

FIG. 7A provides a schematic diagram of the construct using Sif3c to drive the Bar gene which encodes phosphinothricin N-acetyltransferase. The Sif3c sequence was inserted upstream of Bar gene to initiate the expression of Bar. LB: Left border. RB: right border. Bar: phosphinothricin N-acetyltransferase gene. NOS term: nos terminator. FIG. 7B shows seeds collected from *Arabidopsis* transformed with *Agrobacterium* harboring Sif3c/Bar that were grown for 2 weeks, followed by spray of phosphinothricin (PPT). Photographs of the results were taken before and after spraying plants with phosphinothricin.

FIGS. 8A-8C show Sif3abc activity in *Tobacum Nicotiana* (common tobacco). FIG. 8A shows expression in one week old transgenic tobacco seedlings harboring Sif3abc/GUS. Sif3a-driven GUS expression was only observed in leaves. FIG. 8B shows expression in three week old transgenic tobacco seedlings harboring Sif3abc/GUS. FIG. 8C shows histochemical GUS-staining of different tissues harvested from florescent transgenic tobacco harboring Sif3abc/GUS. GUS staining was observed only in leaves, but not in roots, stems or flowers.

FIG. 9 shows GUS expression in *Agrostis stolonifera* (creeping bentgrass) under control of the Sif3 promoter in leaves (left panel) versus roots (right panel). Arrow points to the blue spots indicating expression of the GUS gene.

DETAILED DESCRIPTION OF THE INVENTION

Figure 1A:
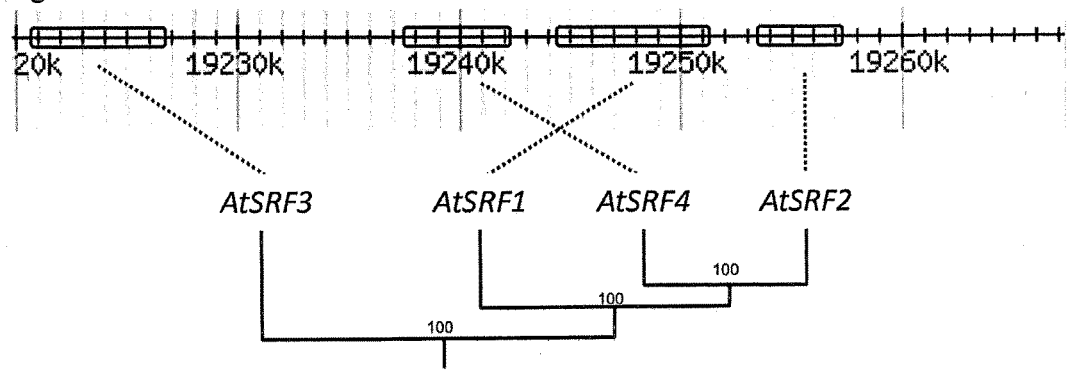
FIGS. 1A-1C show genomic organization of the AtSIF gene cluster on *Arabidopsis* chromosome and analysis of AtSIF3 protein and the nucleic acid encoding the protein.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications and patent applications mentioned in this specification are indicative of the level of skill of those skilled in the art that this invention pertains. Further, publications, patent applications, patents, and other references mentioned herein are incorporated by reference in their entireties for the teachings relevant to the sentence and/or paragraph in which the reference is presented.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, refers to variations of 20%, 110%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim and those that do not materially alter the basic and novel characteristic(s)" of the claimed invention. Thus, the term "consisting essentially of" when used in a claim of this invention is not intended to be interpreted to be equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total often or less additional nucleotides or amino acids includes the total number of additional nucleotides or amino acids on both ends added together.

It will be understood that, although the terms "first," "second," etc. may be used herein to describe various elements, these elements should not be limited by these terms. These terms are only used to distinguish one element from another. Thus, a "first" element (e.g., a first promoter sequence) as described herein could also be termed a "second" element (e.g., a second promoter sequence) without departing from the teachings of the present invention.

With respect to nucleic acids, the term "exogenous" refers to a nucleic acid molecule that is not in the natural genetic background of the cell/organism in which it resides (e.g., exogenous to the host cell and/or comprising regulatory sequences that are exogenous, and/or is located in a different position in the genome than as found in nature). In some embodiments, an exogenous nucleic acid molecule can comprise one or more nucleotide sequences that are not found in the natural genetic background of the cell/organism into which the exogenous nucleic acid molecule is introduced. In some embodiments, an exogenous nucleic acid molecule can comprise one or more additional copies of a nucleotide sequence that is/are endogenous to the cell/organism. In some embodiments, an exogenous nucleic acid molecule can comprise a nucleotide sequence that is endogenous to the cell/organism but is not in its natural genetic context in the cell/organism into which it is introduced.

As used herein, "heterologous" refers to a nucleic acid molecule or polynucleotide that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, and/or under the control of different regulatory sequences than that found in the native state of the nucleic acid molecule.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA (e.g., RNAi, siRNA, miRNA, and the like).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" or "endogenous" nucleotide sequence is a nucleotide sequence naturally associated with a host cell into which it is introduced.

The terms "increase," "increasing," "increased," "enhance," "enhanced," "enhancing," and "enhancement" (and grammatical variations thereof), as used herein, describe an elevation of at least about 20%, 25%, 30%, 35%, 40%, 45%, 50%, 75%, 100%, 125%, 150%, 175%, 200%, 350%, 300%, 350%, 400%, 450%, 500% or more) as compared to a control. Thus, for example, the expression of a heterologous polynucleotide of interest may be increased in the leaves of a transgenic plant comprising said heterologous polynucleotide of interest operably linked to a nucleotide sequence of this invention as compared to a plant not comprising said heterologous polynucleotide of interest operably linked to a nucleotide sequence of this invention.

As used herein, the terms "reduce," "reduced," "reducing," "reduction," "diminish," "suppress," and "decrease" and similar terms refer to a reduction of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5% or more, as compared to a control. In some embodiments, the reduction results in no or essentially no activity (i.e., an insignificant or undetectable amount of activity).

As used herein, the terms "modulating," "modulate," "modulates" or grammatical variations thereof, means an alteration in the expression of a heterologous polynucleotide of interest by increasing or reducing its expression or by altering its expression patterns. Thus, the expression of a heterologous polynucleotide of interest, for example, can be modulated by operably linking said heterologous polynucleotide of interest to a nucleotide sequence of this invention (e.g., (a) a nucleotide sequence of any one of SEQ ID NOs:1-3, or SEQ ID NOs:14-37 (e.g., SEQ ID NOs:1, 2, 3, 14, 15, 16, 17, 18, 19, 20, 21, 22, 23, 24, 25, 26, 27, 28, 29, 30, 31, 32, 33, 34, 35, 36, 37); (b) a nucleotide sequence having at least 70% identity to any one of the nucleotide sequences of (a); (c) a functional fragment of a nucleotide sequence of any one of (a) to (b): or any combination of (a) to (c)).

In some embodiments, the recombinant nucleic acid molecules, and/or nucleotide sequences of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature (i.e., non-naturally occurring). An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs and as such is non-naturally occurring. A polynucleotide is also isolated (e.g., non-naturally occurring) if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences of the invention and their encoded functional nucleic acids are "isolated" or "non-naturally occurring" in that, by the hand of man, they exist apart from their native environment and therefore are not products of nature, however, in some embodiments, they can be introduced into and exist in a recombinant host cell.

Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

Also as used herein, the terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein, a "functional fragment" of a polynucleotide or a polypeptide is one that substantially retains at least one biological activity normally associated with that polynucleotide (e.g., promoter activity) or polypeptide (e.g., target protein binding). In particular embodiments, the "functional fragment" substantially retains all of the activities possessed by the unmodified polynucleotide or polypeptide. By "substantially retains" biological activity, it is meant that the polynucleotide or polypeptide retains at least about 20%, 30%, 40%, 50%, 60%, 75%, 85%, 90%, 95%, 97%, 98%, 99%, or more, of the biological activity of the native polynucleotide or polypeptide (and can even have a higher level of activity than the native polynucleotide or polypeptide). A "non-functional" polynucleotide or polypeptide is one that exhibits little or essentially no detectable biological activity normally associated with the polynucleotide or polypeptide (e.g., at most, only an insignificant amount, e.g., less than about 10%, or even 5%). Biological activities such as promoter activity can be measured using assays that are well known in the art and as described herein.

An exemplary function of a fragment of a nucleotide sequence of this invention may be the ability to confer tissue specific expression.

As used herein, the term "functional RNA" refers to an RNA molecule that does not encode a protein and provide a functional activity as an RNA molecule. Examples include, without limitation, RNAi, microRNA, antisense RNA, and ribozymes.

In some aspects, nucleic acids of the invention may encode any suitable epitope tag, including, but not limited to, poly-Arg tags (e.g., RRRRR, SEQ ID NO:4, and RRRRRR, SEQ ID NO:5) and poly-His tags (e.g., HHH-HHH, SEQ ID NO:6). In some embodiments, the nucleic acid comprises a nucleotide sequence encoding a poly-Arg tag, a poly-His tag, a FLAG tag (i.e., DYKDDDDK, SEQ ID NO:7), a Strep-tag II™ (GE Healthcare, Pittsburgh, Pa., USA) (i.e., WSHPQFEK, SEQ ID NO:8), and/or a c-myc tag (i.e., EQKLISEEDL, SEQ ID NO:9).

In some embodiments of the invention, nucleotide sequences having significant sequence identity to the nucleotide sequences of the invention are provided. "Significant sequence identity" or "significant sequence similarity" means at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identity or similarity with another nucleotide sequence. Thus, in additional embodiments, "significant sequence identity" or "significant sequence similarity" means a range of about 70% to about 100%, about 75% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, and/or about 99% to about 100% identity or similarity with another nucleotide sequence. Therefore, in some embodiments, a nucleotide sequence of the invention is a nucleotide sequence that has significant sequence identity to the nucleotide sequence of any of SEQ ID NOs:1-3 or SEQ ID NOs:14-37.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of this invention has a significant sequence identity (e.g., at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to the nucleotide sequences of the invention.

A homologue as described herein can be utilized with any composition or method of the invention, alone or in combination with one another and/or with one or more nucleotide sequences or polypeptide sequences of the invention.

Thus, in one embodiment, the invention provides a nucleic acid molecule comprising, consisting essentially of, or consisting of one or more nucleotide sequences of the invention and/or one or more homologues of any nucleotide sequence of the invention.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987): and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical" or "significantly identical," in the context of two nucleic acid molecules, nucleotide sequences or protein sequences, refers to two or more sequences or subsequences that have at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of the invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant pest, reducing the growth of a nematode plant pest, reducing nematode cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues: always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see. e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

In some representative embodiments, two nucleotide sequences considered to be substantially complementary hybridize to each other under stringent conditions, optionally under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1.times. to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60.degree. C. Exemplary high stringency conditions include hybridization in 50% formamide, 1 M NaCl, 1% SDS at 37° C., and a final wash in 0.1×SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

A "chimeric gene" is a recombinant nucleic acid molecule in which a promoter or other regulatory nucleotide sequence is operatively associated with a nucleotide sequence that codes for a functional RNA, or an mRNA that is expressed as a protein, such that the regulatory nucleotide sequence is able to regulate transcription or expression of the associated nucleotide sequence. The regulatory nucleotide sequence of the chimeric gene is not normally operatively linked to the associated nucleotide sequence as found in nature.

As used herein, "expression cassette" means a nucleic acid molecule comprising a nucleotide sequence of interest, wherein said nucleotide sequence is operatively associated with at least a control sequence (e.g., a promoter). Thus, some embodiments of the invention provide expression cassettes designed to express at least one heterologous polynucleotide of interest. In this manner, for example, at least one heterologous polynucleotide of interest operably linked to one or more nucleotide sequences of the invention (e.g., (a) a nucleotide sequence of any one of SEQ ID NOs:1-3, or SEQ ID NOs:14-37; (b) a nucleotide sequence having at least 70% identity to any one of the nucleotide sequences of (a): (c) a functional fragment of a nucleotide sequence of any one of (a) to (b); or any combination of (a) to (c)) can be provided in an expression cassette for expression of said at least one heterologous polynucleotide of interest in an organism or cell thereof (e.g., a plant, plant part and/or plant cell). In some embodiments, an expression cassette may comprise a nucleotide sequence of any one of SEQ ID NOs:18-37 operably linked (fused) to a heterologous promoter and to at least one heterologous polynucleotide of interest.

An expression cassette comprising a recombinant nucleic acid molecule of the invention may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the heterologous polynucleotides of interest operatively linked to the nucleotide sequences of the invention, an expression cassette of the invention can also include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences can include, but are not limited to, promoters, enhancers, introns, translation leader sequences, transcription and translation termination signals, and polyadenylation signal sequences. In representative embodiments, a nucleotide sequence of SEQ ID NOs:18-37 can be operably linked (fused) to a heterologous promoter, thereby modifying the expression pattern of the operably linked heterologous promoter and providing a modified expression pattern of a heterologous polypeptide of interest that may be operably linked to the heterologous promoter and nucleotide sequence of any one of SEQ ID NOs:18-37. Thus, in some embodiments, the nucleotide sequences of SEQ ID NOs:18-37 can act as regulatory sequences that modify the pattern of expression of an operably linked heterologous promoter and an operably linked heterologous polynucleotide sequence of interest. In representative embodiments, the nucleotide sequences of SEQ ID NOs:18-37 have little or no promoter activity but when fused (operably linked) to a heterologous promoter that normally provides expression in roots, any one of the nucleotide sequences of SEQ ID NOs:18-37 that may be fused to the heterologous promoter can inhibit root expression of a heterologous polynucleotide of interest that may also be operably linked to the heterologous promoter. In some embodiments, the heterologous promoter may be a constitutive promoter.

As used herein, the term "promoter" refers to a region of a nucleotide sequence that provides signals for the expression of a nucleotide sequence operatively associated with the promoter. This may include sequences to which an RNA polymerase binds, but is not limited to such sequences and can include regions to which other regulatory proteins bind, together with regions involved in the control of protein translation and can also include coding sequences. Furthermore, a "promoter" of this invention is a promoter (e.g., a nucleotide sequence) capable of initiating transcription of a nucleic acid molecule in a cell of a plant.

A number of non-translated leader sequences derived from viruses are known to enhance gene expression. Specifically, leader sequences from Tobacco Mosaic Virus (TMV, the "(ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711: and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4: Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operatively linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons. In addition, a coding sequence's native transcription terminator can be used.

A polynucleotide encoding a signal sequence can be operatively linked to a nucleic acid molecule of the present invention to direct the nucleic acid molecule into a cellular compartment. In this manner, the expression cassette will comprise a nucleic acid molecule of the present invention operatively linked to a nucleotide sequence for the signal sequence. The signal sequence may be operatively linked at the N- or C-terminus of the nucleic acid molecule.

For purposes of the invention, the regulatory sequences or regions can be native/endogenous to the plant, plant part and/or plant cell and/or the regulatory sequences can be native/endogenous in relationship to the other regulatory sequences. Alternatively, the regulatory sequences may be heterologous to the plant (and/or plant part and/or plant cell) and/or to each other (i.e., the regulatory sequences). Thus, for example, a translation termination sequence can be heterologous when it is operatively linked to a polynucleotide from a species different from the species from which the polynucleotide was derived. Alternatively, a translation termination sequence can also be heterologous to a selected nucleotide sequence if the translation termination sequence is from the same species from which the heterologous polynucleotide of interest is derived, but one or both (i.e., translation termination sequence and/or heterologous polynucleotide of interest) are substantially modified from their original form and/or genomic locus, and/or the translation termination sequence is not the native translation termination sequence for the operably linked polynucleotide.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a nucleotide sequence of the invention in operative association with a heterologous polynucleotide of interest would be capable of effecting the expression of that heterologous polynucleotide of interest. In some embodiments, a nucleotide sequence of the invention can be operably linked to a heterologous polynucleotide of interest for expression of that heterologous polynucleotide of interest. In some embodiments, a nucleotide sequence of the invention can be operably linked to a promoter and to a heterologous polynucleotide of interest for expression of that heterologous polynucleotide of interest. Methods of operably linking polynucleotides including promoters and other regulatory elements to polynucleotides of interest are well known (see e.g., Glick B R, Pasternak J J, Patten C L (2010) *Molecular Biotechnology: Principles and Applications of Recombinant DNA*. American Society for Microbiology Press, Washington, D.C.: and Sambrook J, Fritsch E F, Maniatis T (1989) *Molecular cloning: a laboratory manual*. Cold Spring Harbor Laboratory Press, Cold Spring Harbor, N.Y.)

The regulatory sequences (including the nucleotide sequences of the invention and heterologous promoters) need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188): a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts*, 18th Stadler Genetics Symposium (Gustafson & Appels eds., Plenum Press 1988)): a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741): a nucleotide sequence encoding xylE that encodes a catechol dioxygenase (Zukowsky et al. (1983) *Proc. Natl. Acad. Sci. USA* 80:1101-1105): a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268): or a nucleotide sequence encoding green fluorescent protein (Niedz et al. (1995) *Plant Cell Reports* 14:403-406). One of skill in the art is capable of choosing a suitable selectable marker for use in an expression cassette of the invention.

In addition to expression cassettes, the recombinant nucleic acid molecules, nucleotide sequences and heterologous polynucleotides of interest described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of plants and other organisms are well known in the art. Non-limiting examples of general classes of vectors include a viral vector including but not limited to an adenovirus vector, a retroviral vector, an adeno-associated viral vector, a plasmid vector, a phage vector, a phagemid vector, a cosmid, a fosmid, a bacteriophage, or an artificial chromosome. The selection of a vector will depend upon the preferred transformation technique and the target species for transformation. Accordingly, in further embodiments, a recombinant nucleic acid molecule of the invention can be comprised within a recombinant vector. The size of a vector can vary considerably depending on whether the vector comprises one or multiple expression cassettes (e.g., for molecular stacking). Thus, a vector size can range from about 3 kb to about 30 kb. Thus, in some embodiments, a vector is about 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, or any range therein, in size. In some particular embodiments, a vector can be about 3 kb to about 10 kb in size.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein. "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

In some embodiments, the invention provides transformed host cells and transformed organisms comprising the transformed host cells, wherein the host cells and organisms are transformed with one or more recombinant nucleic acid molecules/nucleotide sequences of the invention. In some embodiments, the host cell or organism comprising the recombinant nucleic acid molecules/nucleotide sequences of the invention may be a bacterial cell or bacterium. In representative embodiments, the host cell and/or organism comprising the recombinant nucleic acid molecules/nucleotide sequences of the invention may be a plant cell, plant or plant part.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, in some embodiments, a plant cell of the invention is stably transformed with a nucleic acid molecule of the invention. In other embodiments, a plant of the invention is transiently transformed with a nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended the introduced polynucleotide is stably incorporated into the genome of the cell, and thus the cell is stably transformed with the polynucleotide.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbant assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

As used herein, "tissue specific expression" means that a heterologous polynucleotide of interest operably linked to a nucleotide sequence of this invention is expressed in particular tissues rather than in all tissues of a plant or plant part. In some aspects, "tissue specific expression" means that the heterologous polynucleotide of interest operably linked to a nucleotide sequence of this invention is expressed predominantly in the leaves, stems, shoots, stigma, petals, sepals and the like and is not expressed or has limited expression in at least roots, anthers, seeds, siliques, and seed pods. Thus, in some aspects, about 95% to 100% (e.g., 95%, 96%, 97%, 98%, 99%, 100%, and/or any range and/or value therein) of the heterologous polynucleotide of interest is expressed in the leaves, stems, shoots, stigma, petals, sepals and the like and about 0% to 5% (e.g., 0%, 1%, 2%, 3%, 4%, 5%, and/or any range and/or value therein) of the heterologous polynucleotide of interest is expressed in the roots, anthers, seeds, siliques, and/or seed pods. In some embodiments, no expression of a heterologous polynucleotide of interest occurs in roots, anthers, seeds, siliques, and/or seed pods when the heterologous polynucleotide of interest is operably linked to a nucleotide sequence of this invention.

In some embodiments, a nucleotide sequence of the invention (e.g., one or more of the nucleotide sequences of (a) a nucleotide sequence of any one of SEQ ID NOs:1-3, or SEQ ID NOs:14-37; (b) a nucleotide sequence having at least 70% identity to any one of the nucleotide sequences of (a): (c) a functional fragment of a nucleotide sequence of any one of (a) to (b); or any combination of (a) to (c)) can be introduced into a cell by any method known to those of skill in the art. In some embodiments, a nucleotide sequence of the invention can be operably linked to a heterologous promoter, thereby modifying the expression pattern of the heterologous promoter. In other embodiments, a nucleotide sequence of the invention can be operably linked to a heterologous polynucleotide of interest for expression of the heterologous polynucleotide of interest. In further embodiments, a nucleotide sequence of the invention can be operably linked to a heterologous promoter and to a heterologous polynucleotide of interest for expression of the heterologous polynucleotide of interest.

In some embodiments of the invention, transformation of a cell comprises nuclear transformation. In other embodiments, transformation of a cell comprises plastid transformation (e.g., chloroplast transformation).

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson. J. E., Eds. (CRC Press, Inc., Boca Raton, 1993), pages 67-88) and Rakowoczy-Trojanowska (*Cell. Mol. Biol. Lett.* 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando. Vol. I (1984), and Vol. II (1986)). Methods of selecting for transformed transgenic plants, plant cells and/or plant tissue culture are routine in the art and can be employed in the methods of the invention provided herein.

Likewise, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, the respective nucleotide sequences can be assembled as part of a single nucleic acid construct/molecule, or as separate nucleic acid constructs/molecules, and can be located on the same or different nucleic acid constructs/molecules. Accordingly, the nucleotide sequences can be introduced into a cell in a single transformation event, in separate transformation events, or, for example, in plants, as part of a breeding protocol.

In some embodiments of this invention, the introduced nucleic acid molecule may be maintained in the plant cell stably if it is incorporated into a non-chromosomal autonomous replicon or integrated into the plant chromosome(s). Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule can be present in a plant expression cassette.

Tissue specific promoters are very useful in the agriculture industry because, for example, their use may reduce the accumulation of heterologous proteins or final metabolites in, for example, fruits or seeds of transgenic plants, while not affecting the expression of heterologous polypeptides of interest such as polypeptides encoding herbicide- or insect-resistance genes in the other tissues. The present inventors have identified and isolated a new tissue specific promoter Sif3 cloned from *Arabidopsis* that exhibits a stronger activity than CaMV 35s and maize Ubiquitin promoter in, for example, leaf tissue, while having very low activity or no activity in, for example, root, anther, siliques, seed pods, seeds and the like. Further identified are fragments of the Sif3 promoter, that are useful in modulating expression of heterologous polynucleotides of interest in plants.

Thus, in some aspects, the present invention provides recombinant nucleic acid molecules comprising nucleotide sequences of the invention encoding promoters and fragments thereof that can drive tissue specific expression in plants and parts thereof into which the recombinant nucleic acids are introduced.

In some aspects, the present invention provides a recombinant nucleic acid molecule comprising, consisting essentially of, or consisting of: (a) a nucleotide sequence of any one of SEQ ID NOs:1-3, or SEQ ID NOs:14-17, or any combination thereof; (b) a nucleotide sequence having at least 70% identity to any one of the nucleotide sequences of (a); (c) a functional fragment of a nucleotide sequence of any one of (a) to (b); or any combination of (a) to (c), above, wherein the nucleotide sequence of (a) and/or (b) and/or the functional fragment of (c) is operably linked to at least one heterologous polynucleotide of interest (e.g., at least one nucleotide sequence encoding a polypeptide or a functional nucleic acid), thereby producing a plant and/or plant part expressing the at least one heterologous polynucleotide of interest. In some embodiments, the recombinant nucleic acid molecules of the invention may be comprised in expression cassettes and/or vectors. The recombinant nucleic acid molecule, nucleotide sequences, expression cassettes and/or heterologous polynucleotides of interest may be codon optimized. In some embodiments, the expression pattern of the heterologous polynucleotide of interest can be tissue specific.

In some aspects, the present invention provides a recombinant nucleic acid molecule comprising: (a) a nucleotide sequence of any one of SEQ ID NOs:18-37, or any combination thereof; (b) a nucleotide sequence having at least 70% identity to any one of the nucleotide sequences of (a); (c) a functional fragment of a nucleotide sequence of any one of (a) to (b); or any combination of (a) to (c), above, wherein the nucleotide sequence of (a) and/or (b) and/or the functional fragment of (c) is operably linked to a heterologous promoter, thereby modifying the tissue specificity of the heterologous promoter. Thus, the nucleotide sequence of (a) and/or (b) and/or the functional fragment of (c) can confer on a heterologous promoter a different expression pattern from that of the wild type heterologous promoter (the heterologous promoter that is not operably linked to a nucleotide sequence of the invention: e.g., SEQ ID NOs: 18-37). In some embodiments, the nucleotide sequence of (a) and/or (b) and/or the functional fragment of (c) further may be operably linked to at least one heterologous polynucleotide of interest (e.g., at least one nucleotide sequence encoding a polypeptide or a functional nucleic acid), thereby expressing the heterologous polynucleotide of interest in a tissue specific manner or in a manner that is modified from the expression pattern that is conferred using the heterologous promoter that is not operably linked to the nucleotide sequence of (a) and/or (b) and/or the functional fragment of (c). In some embodiments, the recombinant nucleic acid molecule of the invention may be comprised in expression cassettes and/or vectors. In some aspects, the recombinant nucleic acid molecule, nucleotide sequences, expression cassettes and/or heterologous polynucleotides of interest may be codon optimized. In some embodiments, the heterologous promoter may be a constitutive promoter, wherein the expression pattern of the heterologous promoter is modified such that it now confers tissue specific expression. Thus, in some embodiments, when a heterologous promoter is operably linked to (a) a nucleotide sequence of any one of SEQ ID NOs:18-37, or any combination thereof: (b) a nucleotide sequence having at least 70% identity to any one of the nucleotide sequences of (a); (c) a functional fragment of a nucleotide sequence of any one of (a) to (b): or any combination of (a) to (c), the expression pattern of the heterologous promoter is modified to be tissue specific.

A heterologous polynucleotide of interest can be any polynucleotide that may be used to confer a desired trait or phenotype on a plant. Thus, for example, a heterologous polynucleotide of interest can be a polynucleotide encoding a polypeptide or a functional nucleic acid (e.g., regulatory sequences, RNAi, anti-sense RNA, microRNA, siRNA and the like), which can confer a desired characteristic. Such desirable characteristics may include, but are not limited to, herbicide resistance, abiotic stress resistance/tolerance, increased yield, increased biomass, pest resistance (e.g., insect, fungal, viral, nematode resistance and the like), improved nutrient composition, improved efficiency in uptake and use of nitrogen and in use of other macro and micro minerals, improved digestibility, decreased lignin content, phytoremediation, and the like.

In further aspects, the recombinant nucleic acid molecules/nucleotide sequences of the invention can be comprised in an expression cassette or vector as described herein. In some embodiments, an expression cassette of the invention can further comprise at least one regulatory nucleotide sequence, optionally at least one intron, at least one exon, a TMV omega translation enhancer and/or a Kozak sequence.

The present invention further provides cells and/or organisms (or parts thereof) comprising at least one nucleotide sequence of the invention or at least one recombinant nucleic acid molecule, expression cassette or vector comprising said at least one nucleotide sequence of the invention, optionally wherein the cells and/or organisms may be plant, bacterial, and/or fungal.

In some aspects, any nucleotide sequence, recombinant nucleic acid molecule, functional fragment and/or expression cassette of this invention can be codon optimized for expression in any plant, bacterial or fungal species. Codon optimization is well known in the art and involves modification of a nucleotide sequence for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in representative embodiments of the invention, the nucleotide sequences and/or recombinant nucleic acid molecules of this invention and other components (including but not limited to the regulatory sequences such as promoter sequences and terminator sequences, and the like) can be codon optimized for expression in any particular plant species of interest. In some embodiments, the codon optimized nucleotide sequences of any one of SEQ ID NOs:1-3, or SEQ ID NOs:14-37 may have about 70% to about 99% identity to the nucleotide sequences of any one of SEQ ID NOs:1-3, or SEQ ID NOs:14-37.

In representative embodiments, transgenic plant cells, transgenic plants, and/or transgenic plant parts are provided, said transgenic plant cells, transgenic plants, and/or transgenic plant parts comprising, consisting essentially of, or consisting of a recombinant nucleic acid molecule of the invention (i.e., transgenic plant cells, plants and/or plant parts comprising a recombinant nucleic acid that comprises (a) a nucleotide sequence of SEQ ID NOs:1-3, or SEQ ID NOs:14-37, (b) a nucleotide sequence having at least 70% identity to the nucleotide sequence of SEQ ID NOs:1-3, or SEQ ID NOs:14-37, a functional fragment of a nucleotide sequence of any one of (a) and/or (b), or any combination thereof). In some embodiments, the transgenic plant cells, plants and/or plant parts of the invention can comprise a recombinant nucleic acid of the invention in an expression cassette or vector, wherein the recombinant nucleic acid comprises at least one heterologous gene of interest and/or a heterologous promoter operably linked to (a) a nucleotide sequence of SEQ ID NOs:1-3, or SEQ ID NOs:14-37, (b) a nucleotide sequence having at least 70% identity to the nucleotide sequence of SEQ ID NOs:1-3, or SEQ ID NOs: 14-37, a functional fragment of a nucleotide sequence of any one of (a) and/or (b), or any combination thereof. The transgenic plant cell, plant and/or plant part of the invention can be stably transformed or transiently transformed.

Further provided are methods of producing such transgenic plant cells, transgenic plants, and/or transgenic plant parts.

Accordingly, in one aspect, the invention provides a method of expressing at least one heterologous polynucleotide of interest in a plant and/or plant part, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NOs:1-3, or SEQ ID NOs:14-17, (b) a nucleotide sequence having at least 70% identity to any one of SEQ ID NOs:1-3, or SEQ ID NOs:14-17; (c) a functional fragment of a nucleotide sequence of (a) or (b), or any combination of (a) to (c), wherein the nucleotide sequence of (a) and/or (b) and/or the functional fragment of (c) is operably linked to at least one heterologous polynucleotide of interest, thereby expressing in the plant and/or plant part the at least one heterologous polynucleotide of interest. In some aspects, the expression can be tissue specific. In some embodiments, the tissue specific expression comprises expression in most plant tissues but not in root, anther, silique, seed pod, and/or seed. In some embodiments, the at least one heterologous polynucleotide of interest is not expressed in the roots. In some embodiments, the at least one heterologous polynucleotide of interest is not expressed in the roots, anthers, siliques, seed pods, or seeds. In some embodiments, the at least one heterologous polynucleotide of interest is not expressed in anthers or seeds. In some embodiments, the at least one heterologous polynucleotide of interest is not expressed in seeds. In some embodiments, the at least one heterologous polynucleotide of interest is not expressed or has limited expression (e.g., about 5% or less) in the roots and seeds.

In some aspects, the invention provides a method of expressing at least one heterologous polynucleotide of interest in a plant and/or plant part, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NOs:18-37, (b) a nucleotide sequence having at least 70% identity to any one of SEQ ID NOs: 18-37; (c) a functional fragment of a nucleotide sequence of (a) or (b), or any combination of (a) to (c), and the nucleotide sequence of (a) and/or (b) and/or the functional fragment of (c) is operably linked to a heterologous promoter and to at least one heterologous polynucleotide of interest, thereby expressing in the plant and/or plant part the at least one heterologous polynucleotide of interest. In some aspects, the expression can be tissue specific. In some embodiments, the at least one heterologous polynucleotide of interest is not expressed in the roots.

In a further aspect, the invention provides a method of expressing at least one heterologous polynucleotide of interest in a plant and/or plant part in a tissue specific manner, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NOs:1-3, or SEQ ID NOs:14-17, (b) a nucleotide sequence having at least 70% identity to any one of SEQ ID NOs:1-3, or SEQ ID NOs: 14-17: (c) a functional fragment of a nucleotide sequence of (a) or (b), or any combination of (a) to (c), and the nucleotide sequence of (a) and/or (b) and/or the functional fragment of (c) is operably linked to at least one heterologous polynucleotide of interest, thereby expressing in a plant and/or plant part the at least one heterologous polynucleotide of interest in a tissue specific manner. In some aspects, a "tissue specific manner" means that the heterologous polynucleotide of interest is expressed in most plant tissues but not in roots, anthers, siliques, seed pods, or seeds.

In some aspects, the invention provides a method of expressing at least one heterologous polynucleotide of interest in a plant and/or plant part in a tissue specific manner, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NOs:18-37, (b) a nucleotide sequence having at least 70% identity to any one of SEQ ID NOs:18-37: (c) a functional fragment of a nucleotide sequence of (a) or (b), or any combination of (a) to (c), and the nucleotide sequence of (a) and/or (b) and/or the functional fragment of (c) is operably linked to a heterologous promoter and to at least one heterologous polynucleotide of interest, thereby expressing in a plant and/or plant part the at least one heterologous polynucleotide of interest in a tissue specific manner. In some aspects, the at least one heterologous polynucleotide of interest is expressed in most tissues but not in roots.

In a further aspect, the invention provides a method of expressing at least one heterologous polynucleotide of interest in a plant and/or plant part in most tissues but not in roots, anthers, siliques, seed pods, and seeds, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NO:1, (b) a nucleotide sequence having at least 70% identity to any one of SEQ ID NO:1; (c) a functional fragment of a nucleotide sequence of (a) or (b), or any combination of (a) to (c), and the nucleotide sequence of (a) and/or (b) and/or the functional fragment of (c) is operably linked to at least one heterologous polynucleotide of interest, thereby expressing in a plant and/or plant part the at least one heterologous polynucleotide of interest in most tissues but not in roots, anthers, siliques, seed pods, and seeds.

In some aspects, the invention provides a method of expressing at least one heterologous polynucleotide of interest in a plant and/or plant part in most tissues but not in anthers and seeds, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NO:2 and/or SEQ ID NO:3, (b) a nucleotide sequence having at least 70% identity to any one of SEQ ID NO:2 and/or SEQ ID NO:3: (c) a functional fragment of a nucleotide sequence of (a) or (b), or any combination of (a) to (c), and the nucleotide sequence of (a) and/or (b) and/or the functional fragment of (c) is operably linked to a heterologous promoter and to at least one heterologous polynucleotide of interest, thereby expressing in a plant and/or plant part the at least one heterologous polynucleotide of interest in most tissues but not in anthers and seeds. In some embodiments, the expression conferred by the nucleotide sequence of SEQ ID NO:3 may be considered constitutive expression.

In a further aspect, the invention provides a method of expressing at least one heterologous polynucleotide of interest in a plant and/or plant part in most tissues but not in seeds, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NO:14 and/or SEQ ID NO:17, (b) a nucleotide sequence having at least 70% identity to any one of SEQ ID NO:14 and/or SEQ ID NO:17; (c) a functional fragment of a nucleotide sequence of (a) or (b), or any combination of (a) to (c), and the nucleotide sequence of (a) and/or (b) and/or the functional fragment of (c) is operably linked to at least one heterologous polynucleotide of interest, thereby expressing in a plant and/or plant part the at least one heterologous polynucleotide of interest in most tissues but not in seeds. In some embodiments, the expression conferred by the nucleotide sequence of SEQ ID NO:14 and/or SEQ ID NO:17 may be considered constitutive expression.

In some aspects, the invention provides a method of expressing at least one heterologous polynucleotide of interest in a plant and/or plant part in most tissues but not in roots and seeds, comprising: introducing into a plant and/or plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of (a) the nucleotide sequence of any one of SEQ ID NO:15 and/or SEQ ID NO:16, (b) a nucleotide sequence having at least 70% identity to any one of SEQ ID NO:15 and/or SEQ ID NO:16; (c) a functional fragment of a nucleotide sequence of (a) or (b), or any combination of (a) to (c), and the nucleotide sequence of (a) and/or (b) and/or the functional fragment of (c) is operably linked to a heterologous promoter and to at least one heterologous polynucleotide of interest, thereby expressing in a plant and/or plant part the at least one heterologous polynucleotide of interest in most tissues but not in roots and seeds.

In another aspect, the invention provides a method of expressing at least one heterologous polynucleotide of interest in a plant and/or plant part in most tissues but not in roots, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of SEQ ID NOs:18-37, (b) a nucleotide sequence having at least 70% identity to any one of SEQ ID NOs:18-37, (c) a functional fragment of a nucleotide sequence of (a) or (b), or any combination of (a) to (c), and the nucleotide sequence of (a) and/or (b) and/or the functional fragment of (c) is operably linked to a heterologous promoter and at least one heterologous polynucleotide of interest, thereby producing a plant and/or plant part expressing the at least one heterologous polynucleotide of interest in most tissues but not in roots.

In some aspects, the invention provides a method of producing a plant and/or a plant part expressing at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:1-3, or SEQ ID NOs:14-17, (b) a nucleotide sequence having at least 70% identity to any one of SEQ ID NOs:1-3, or SEQ ID NOs:14-17; (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant and/or plant part expressing the at least one heterologous polynucleotide of interest. In some embodiments, the expression pattern of the at least one heterologous polynucleotide of interest may be tissue specific.

In a further aspect, the invention provides a method of producing a plant and/or a plant part expressing at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:18-37, (b) a nucleotide sequence having at least 70% identity to any one of SEQ ID NOs:18-37; (c) a functional fragment of a nucleotide sequence of (a) or (b), or any combination of (a) to (c), above, wherein the nucleotide sequence of (a) and/or (b) and/or the functional fragment of (c) is operably linked to a heterologous promoter and at least one heterologous polynucleotide of interest; thereby producing a plant and/or plant part expressing the at least one heterologous polynucleotide of interest.

In a further aspect, the present invention provides a method of producing a plant and/or a plant part having tissue specific expression of at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:1-3, or SEQ ID NOs:14-17, (b) a nucleotide sequence having at least 70% identity to the nucleotide sequence of any one of SEQ ID NOs:1-3, or SEQ ID NOs:14-17, (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant having tissue specific expression of the at least one heterologous polynucleotide of interest. In some embodiments, the at least one heterologous polynucleotide of interest is not expressed in the roots. In some embodiments, the at least one heterologous polynucleotide of interest is not expressed in the roots, anthers, siliques, seed pods, or seeds. In some embodiments, the at least one heterologous polynucleotide of interest is not expressed in anthers or seeds. In some embodiments, the at least one heterologous polynucleotide of interest is not expressed in seeds. In some embodiments, the at least one heterologous polynucleotide of interest is not expressed or has limited expression (e.g., about 5% or less) in the roots and seeds.

In some aspects, the present invention provides a method of producing a plant and/or a plant part having tissue specific expression of at least one heterologous polynucleotide of interest, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of any one of SEQ ID NOs:18-37, (b) a nucleotide sequence having at least 70% identity to the nucleotide sequence of any one of SEQ ID NOs:18-37, (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant having tissue specific expression of at least one heterologous polynucleotide of interest. In some embodiments, the at least one heterologous polynucleotide of interest is expressed in most plant tissues but is not expressed in at least the roots.

In a further aspect, the present invention provides a method of producing a plant and/or a plant part having expression of at least one heterologous polynucleotide of interest in most tissues but not in roots, anthers, siliques, seed pods, and seeds, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of SEQ ID NO: 1, (b) a nucleotide sequence having at least 70% identity to the nucleotide sequence of SEQ ID NO:1, (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant having expression of the at least one heterologous polynucleotide of interest in most tissues but not in roots, anthers, siliques, seed pods, and seeds.

In some aspects, the present invention provides a method of producing a plant and/or a plant part having expression of at least one heterologous polynucleotide of interest in most tissues but not in anthers and seeds, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of SEQ ID NO:2 and/or SEQ ID NO:3, (b) a nucleotide sequence having at least 70% identity to the nucleotide sequence of SEQ ID NO:2 and/or SEQ ID NO:3, (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant having expression of the at least one heterologous polynucleotide of interest in most tissues but not in anthers and seeds.

In some aspects, the present invention provides a method of producing a plant and/or a plant part having expression of at least one heterologous polynucleotide of interest in most tissues but not in seeds, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of SEQ ID NO:14 and/or SEQ ID NO:17, (b) a nucleotide sequence having at least 70% identity to the nucleotide sequence of SEQ ID NO:14 and/or SEQ ID NO:17, (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant having expression of the at least one heterologous polynucleotide of interest in most tissues but not in seeds.

In some aspects, the present invention provides a method of producing a plant and/or a plant part having expression of at least one heterologous polynucleotide of interest in most tissues but not in roots and seeds, comprising: introducing into a plant and/or plant part a recombinant nucleic acid molecule of the invention, or an expression cassette or vector comprising the recombinant nucleic acid molecule, the recombinant nucleic acid molecule comprising (a) the nucleotide sequence of SEQ ID NO:15 and/or SEQ ID NO:16, (b) a nucleotide sequence having at least 70% identity to the nucleotide sequence of SEQ ID NO:15 and/or SEQ ID NO:16, (c) a functional fragment of a nucleotide sequence of (a) or (b), or any combination of (a) to (c), above, wherein the nucleotide sequence of (a) and/or (b) and/or the functional fragment of (c) is operably linked to at least one heterologous polynucleotide of interest, thereby producing a plant having expression of the at least one heterologous polynucleotide of interest in most tissues but not in roots and seeds.

In another aspect, the present invention provides a method of producing a plant and/or a plant part having expression of at least one heterologous polynucleotide of interest in most tissues but not in roots, comprising: introducing into a plant and/or plant part a recombinant nucleic acid molecule of the invention, or an expression cassette or vector comprising the recombinant nucleic acid molecule, the recombinant nucleic acid comprising (a) the nucleotide sequence of SEQ ID NOs:18-37, (b) a nucleotide sequence having at least 70% identity to any one of SEQ ID NOs: 18-37, (c) a functional fragment of a nucleotide sequence of (a) or (b), or any combination of (a) to (c), wherein the nucleotide sequence of (a) and/or (b) and/or the functional fragment of (c) is operably linked to a heterologous promoter and at least one heterologous polynucleotide of interest, thereby producing a plant having expression of the at least one heterologous polynucleotide of interest in most tissues but not in roots.

In an additional aspect, a method of producing a plant comprising a heterologous nucleotide sequence of interest that is expressed in a tissue specific manner such that it is not expressed in the parts of the plant harvested for human consumption is provided, the method comprising: introducing into a plant and/or a plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of: (a) the nucleotide sequence of SEQ ID NOs: 1-3 or SEQ ID NOs:14-17, (b) a nucleotide sequence having at least 70% identity to the nucleotide sequence of SEQ ID NOs:1-3 or SEQ ID NOs:14-17, (c) a functional fragment of a nucleotide sequence of (a) or (b), or any combination of (a) to (c), wherein the nucleotide sequence of (a) and/or (b) and/or the functional fragment of (c) is operably linked to at least one heterologous polynucleotide of interest to produce a plant or plant part having tissue specific expression of the at least one heterologous polynucleotide of interest such that the at least one heterologous polynucleotide of interest is not expressed in the parts of the plant harvested for human consumption, thereby producing a plant comprising a heterologous nucleotide sequence of interest that is not expressed in the parts of the plant harvested for human consumption. In some embodiments, the plant part produced by the method is regenerated into a plant in which the heterologous polynucleotide of interest is not expressed in the parts of the plant harvested for human consumption. In some embodiments, the seeds, seed capsules, seed pods, siliques, roots, flower parts, fruit, and/or stems are harvested from the plant for human consumption.

In some aspects, a method of producing a plant comprising a heterologous nucleotide sequence of interest that is expressed in a tissue specific manner such that it is not expressed in the parts of the plant harvested for human consumption is provided, the method comprising: introducing into a plant and/or a plant part a recombinant nucleic acid molecule of the invention, or an expression cassette or vector comprising the recombinant nucleic acid molecule, wherein the recombinant nucleic acid molecule comprises a nucleotide sequence comprising, consisting essentially of, or consisting of: (a) the nucleotide sequence of SEQ ID NOs: 18-37, (b) a nucleotide sequence having at least 70% identity to the nucleotide sequence of SEQ ID NOs:18-37, (c) a functional fragment of a nucleotide sequence of (a) or (b), or any combination of (a) to (c), wherein the nucleotide sequence of (a) and/or (b) and/or the functional fragment of (c) is operably linked to a heterologous promoter and at least one heterologous polynucleotide of interest to produce a plant or plant part having tissue specific expression of the at least one heterologous polynucleotide of interest such that at least one heterologous polynucleotide of interest is not expressed in the parts of the plant harvested for human consumption; thereby producing a plant comprising a heterologous nucleotide sequence of interest that is not expressed in the parts of the plant harvested for human consumption. In some embodiments, the plant part produced by the method is regenerated into a plant in which the heterologous polynucleotide of interest is not expressed in the parts of the plant harvested for human consumption. In some embodiments, the roots are harvested from the plant for human consumption.

Further provided herein are the plants, plant parts, and plant cells made by the methods of the invention. Also provided are seeds produced by the plants made by the methods of the invention and plants produced from the seeds, wherein the seeds comprise in their genomes a recombinant nucleic acid of the invention.

In additional aspects, crops comprising a plurality of transgenic plants of the invention are provided. Nonlimiting examples of types of crops comprising a plurality of transgenic plants of the invention include an agricultural field, a golf course, a residential lawn, an ornamental garden, a road side, an athletic field, and/or a recreational field.

As used herein, "plant" means any plant and thus includes, for example, angiosperms, gymnosperms, bryophytes, ferns and/or fern allies. In some embodiments, the plant cell, plant and/or plant part of the invention can be a cell, plant and/or plant part of any plant species. Non-limiting examples of plants of the present invention include turf grasses, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin), radishes, dry bulb onions, rutabaga, eggplant, salsify, escarole, shallots, endive, garlic, spinach, green onions, squash, greens, beet (sugar beet and fodder beet), sweet potatoes, swiss chard, horseradish, tomatoes, turnips, and spices; a fruit and/or vine crop such as apples, apricots, cherries, nectarines, peaches, pears, plums, prunes, cherry, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee, a field crop plant such as clover, alfalfa, evening primrose, meadow foam, corn/maize (field, sweet, popcorn), hops, jojoba, peanuts, rice, safflower, small grains (barley, oats, rye, wheat, etc.), sorghum, tobacco, kapok, a leguminous plant (beans, lentils, peas, soybeans), an oil plant (rape, mustard, poppy, olive, sunflower, coconut, castor oil plant, cocoa bean, groundnut), *Arabidopsis*, a fiber plant (cotton, flax, hemp, jute), lauraceae (cinnamon, camphor), or a plant such as coffee, sugar cane, tea, and natural rubber plants; and/or a bedding plant such as a flowering plant, a cactus, a succulent and/or an ornamental plant, as well as trees such as forest (broad-leaved trees and evergreens, such as conifers), fruit, ornamental, and nut-bearing trees, as well as shrubs and other nursery stock.

In particular embodiments, a plant cell, plant and/or plant part of the invention can be a turfgrass. As used herein, turfgrass includes, but is not limited to, *Sporobolus airiodes, Puccinellia distans, Paspalum notatum, Cynodon dactylon, Buchloe dactyloides, Cenchrus ciliaris, Hordeum californicum, Hordeum vulgare, Hordeum brachyantherum, Agrostis capillaries, Agrostis palustris, Agrostis exerata, Briza maxima, Poa annua, Poa ampla, Poa canbyi, Poa compressa, Poa pratensis, Poa scabrella, Poa trivialis, Poa secunda, Andropogon gerardii, Schizachyruim scoparium, Andropogon hallii, Bromus arizonicus, Bromus carinatus, Bromus biebersteinti, Bromus marginatus, Bromus rubens, Bromus inermis, Buchloe dactyloides, Axonopus fissifolius, Eremochloa ophiuroides, Muhlenbergia rigens, Sporobolus cryptandrus, Sporobolus heterolepis, Tripsacum dactyloides, Festuca arizonica, Festuca rubra* var. *commutate, Festuca rubra* var. *rubra, Festuca megalura, Festuca longifolia, Festuca idahoensis, Festuca elatior, Fescue rubra, Fescue ovina* var. *ovina, Festuca arundinacea, Alopecurus arundinaceaus, Alopecurus pratensis, Hilaria jamesii, Bouteloua eriopoda, Bouteloua gracilis, Bouteloua curtipendula, Deschampsia caespitosa, Oryopsis hymenoides, Sorghastrum nutans, Eragrostis trichodes, Eragrostis curvula, Melica californica, Stipa comate, Stipa lepida, Stipa viridula, Stipa cernua, Stipa pulchra, Dactylis glomerata, Koeleria pyramidata, Calamovilfa longifolia, Agrostis alba, Phalaris arundinacea, Stenotaphrum secundatum, Spartina pectinata, Lolhum multiflorum, Lolium perenne, Leptochloa dubia, Sitanion hystrix, Panicum virgatum, Aristida purpurea, Phleum pretense, Agropyron spicatum, Agropyron cristatum, Agropyron desertorum, Agropyron intermedium, Agropyron trichophorum, Agropyron trachycaulum, Agropyron riparium, Agropyron elongatum, Agropyron smithii, Elymus glaucus, Elymus Canadensis, Elvmus triticoides, Elymus junceus, Zoysia japonica, Zoysia matrella*, and *Zoysia tenuifolia*.

In some embodiments, a plant of the present invention can be soybean, cotton, rice and/or corn.

The present invention further provides a product harvested from a transgenic plant and/or part thereof of the invention, wherein the product comprises the recombinant nucleic acid molecule. Non-limiting examples of a harvested product include a seed, a leaf, a stem, a shoot, a fruit, flower, root, and/or extract. In some embodiments, a processed or post-harvest product produced from the harvested product is provided. Non-limiting examples of a processed product include a protein, an extract, a medicinal product (e.g., artemicin as an antimalarial agent), a biofuel (e.g., ethanol), and/or a fragrance.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1. Material and Methods

We have cloned and characterized a promoter from *Arabidopsis thaliana* named Sif3.

Plant Materials and Maintenance

*Arabidopsis thaliana* was grown on ½ MS plates or in soil in growth chamber under a 16 hr-light/8 hr-dark photoperiod at a temperature of 21° C. in the light and 24° C. in the dark.

Tobacco and creeping bentgrass were grown in soil in a greenhouse under a 12 h-light/12 h-dark photoperiod at a 27° C. temperature.

DNA and RNA Isolation and cDNA Synthesis

Plant genomic DNA was isolated using a cetyltrimethylammonium bromide method previously described (Luo, H., et al., *Molecular Breeding*, 16(2): 185-188 (2005)).

Total RNA samples from two week old *Arabidopsis* plants were extracted with Trizol reagent (Ambion, USA) from 100 mg leaf or root tissues, followed by treatment with RNase-free DNase I (Invitrogen, USA) to remove genomic DNA. Two micrograms of RNA was used for synthesis of the first strand cDNA with reverse transcriptase (Invitrogen, USA) according to the manufacturer's instructions. Synthesized cDNA was used for RT-PCR analysis.

Binary Vector Construction and Bacterial Strains

A 1524 bp fragment of the predicted promoter Sif3abc was amplified from *Arabidopsis* genomic DNA and cloned into the binary vector pSBbar#5-GUS-nos in the upstream of the GUS gene, resulting in the construct Sif3abc/GUS/nos-p35s/bar/nos. The primers used to amplify Sif3abc were the forward primer ACCTAGGCTCGGTAGAGGTCCTGAT-TATATTTC (SEQ ID NO:10) with an AvrII cutting site and the reverse primer ACTCGAGTTACTATG-CAAAGAAGGGATCTGT (SEQ ID NO:11) with an XhoI cutting site.

To generate the 5' end deletion mutation promoter driving GUS cassettes Sif3bc/GUS/nos-p35s/bar/nos and Sif3c/GUS/nos-p35s/bar/nos, similar steps were performed except the forward primer for amplification of Sif3b or Sif3c was switched to ACCTAGGGGAAATAACAGATTGAGAGC (SEQ ID NO:12) or ACCTAGGCAG ATGATTACTTAT-GTCCAC (SEQ ID NO:13), respectively.

A CaMV 35s fragment with BamHI-digested cutting sites at its 5' end and 3' end was ligated to the BamHI-digested of pSBbar#5-GUS-nos in the upstream multiple cloning site of GUS gene to generate 35S/GUS/nos-p35s/bar/nos.

Binary vectors were mobilized into *Agrobacterium tumefaciens* strain LBA4404 by electroporation for plant transformation.

Plants Transformation and Histochemical GUS Staining:

*Arabidopsis thaliana* transformation, tobacco transformation and creeping bent grass transformation were performed with *Agrobacterium* harboring chimeric constructs as previously described (Clough, S. J. and A. F. Bent. *The Plant Journal*. 16(6):735-743 (1998); Horsch, R., et al., *Science* 227:1229-1231 (1985); Luo, H., et al., *Plant Cell Rep*, 22(9):645-652 (2004)).

GUS (β-glucuronidase) activity was assayed by histochemical staining with 1 mM X-Gluc (Biosynth AG, Staad, Switzerland). Plant samples immersed in 100 μl to 10 mL reaction buffer containing X-Gluc were vacuum infiltrated for 10 mins twice, followed by incubation at 37° C. overnight. Prior to photography, plant samples were destained and stored in 70% ethanol (Jefferson et al. *The EMBO Journal* 6(13):3901 (1987)).

Quantitative Measurement of GUS Activity

GUS activity was determined according to previously described methods with minor modification (Jefferson et al. *EMBO J.* 6(13):3901-7 (1987); Francis, K. E. and S. Spiker. *Plant Journal* 41(3):464-477(2005)). A 100 mg plant sample was ground in extraction buffer (50 mM NaHPO$_4$ pH 7.0, 10 mM Na$_2$EDTA, 10 mM 3-mercaptoethanol, 0.1% Triton X-100, 0.1% sarcosyl, 140 μM PMSF) on ice followed by centrifuge for 15 min at 13000 rpm and 8° C. 400 μl supernatant was transferred to a clean 1.5 microcentrifuge tube. 10 μl supernatant was then transferred to 130 μl assay buffer (extraction buffer with 2 mM 4-methylumbelliferyl 3-D-glucuronide as substrate) and incubated in 37° C. under a dark condition for 25 min. Remove 10 μl reaction to 190 μl stop buffer (0.2M Sodium Carbonate, anhydrous) in a 96-well microtitle plate. Fluorescent value of reaction product 4-methylumbelliferyl (4-MU) was measured in a microplate reader at emission wavelength as 480 nm when the excitation wavelength was 360 nm.

The protein concentration was determined following Bradford's method (Bradford, M. M. *Anal Biochem*. 72:248-254 (1976)). The GUS activity was finally expressed in pmols 4-MU/min/μg protein units. Student's t test was used for data analysis. $P<0.05$ was considered to be statistically significant and marked as *. $P<0.01$ was considered to be statistically highly significant and marked as **

Figure 1B:
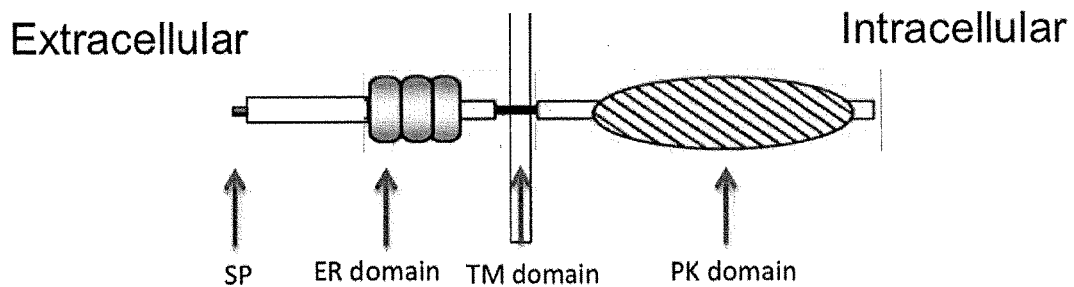
Figure 1C:
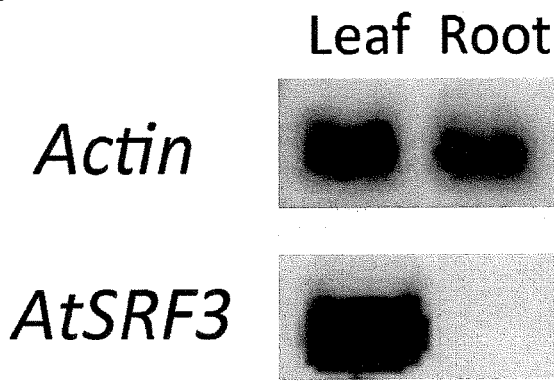

Example 2. Identification, Cloning and Deletion Constructs of the Sif3 Promoter We have identified a novel protein kinase gene family (FIG. 1A). One family member AtSIF3 (FIG. 1B) attracted was of particular interest. AtSIF3 encodes a Leucine-Rich-Repeat Receptor Like protein Kinase (LRR-RLKs), and it is strongly and specifically expressed in *Arabidopsis* leaf tissue (FIG. 1C). This promoter was of interest because of its activity in tissues that, in some instances, may not be used as food or plant product. Therefore, the promoter could be used to drive gene expression in tissues that are not consumed, leaving the tissues that are intended for consumption with little or no expression of the transgene.

Figure 2A:
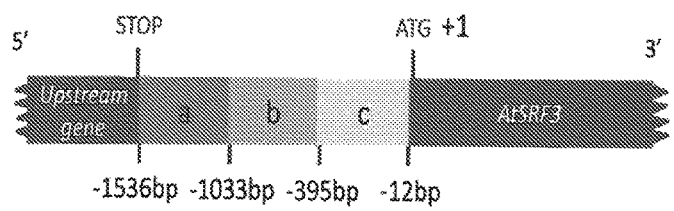
FIG. 2A-2C show the cloning and 5' deletion analyses of AtSIF3 promoter (SEQ ID NO:1) and construction of GUS reporter systems.
Figure 2B:
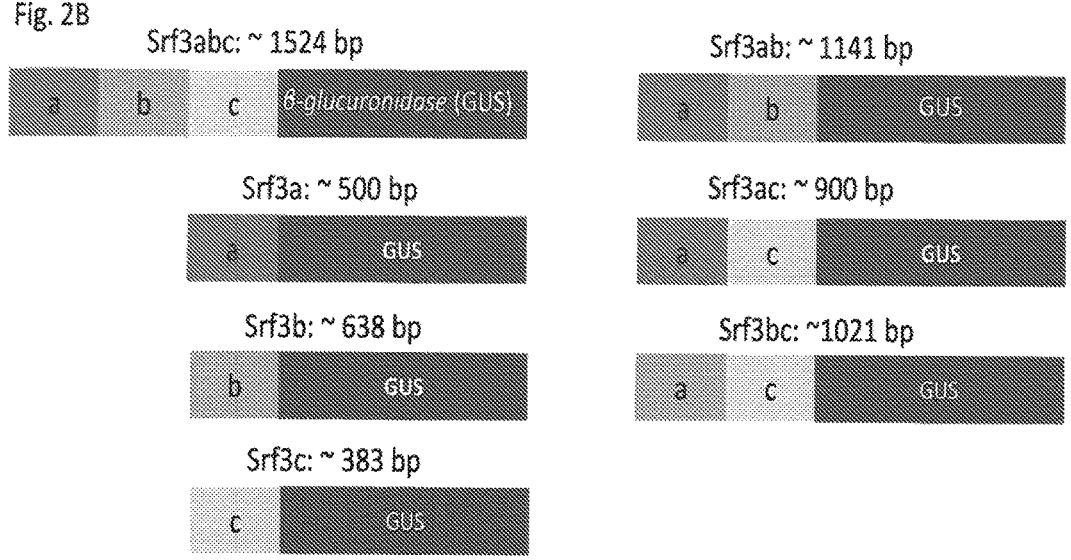
Figure 2C:

To characterize the Sif3 promoter region, we cloned the DNA sequence between the upstream gene and AtSIF3 and named it Sif3abc promoter (FIG. 2). The 1524 bp Sif3abc with 87 bp 5'UTR of AtSIF (from base pair position −1536 to −12). Meanwhile, to further analyze the function of Sif3 promoter region, two 5' end deletion mutations of Sif3abc promoter were also generated, which are 1021 bp Sif3bc (from base pair position −1033 to −12) and 383 bp Sif3c (from base pair position −395 to −12) (FIG. 2). These three promoter sequences, together with CaMV 35S and maize ubiquitin promoters, were placed upstream of a nucleotides sequence encoding GUS in the T-DNA regions of binary vectors to provide a GUS reporter system (FIG. 3) (Jefferson et al. *The EMBO Journal* 6(13):3901 (1987)). The five chimeric constructs were introduced via Agrobacteria-mediated transformation into *Arabidopsis thaliana* to produce stable transgenic plants (Clough, S. J. and A. F. Bent, *The Plant Journal* 16(6): 735-74 (1998)). Polymerase chain reaction (PCR) assays were conducted to screen transgenic plants harboring the chimeric DNA sequence using GUS nucleic acid amplification primers. More than 10 independent events of each line are identified.

Example 3. Activity of Sif3abc Promoter is Leaf Specific and Deletion of 5' End Alters Tissue Specificity To determine the activity pattern of three Sif3 promoters, histochemical GUS staining was performed to analyze the promoter activity in transgenic *Arabidopsis* plants at different developmental stages.

Figure 4A:
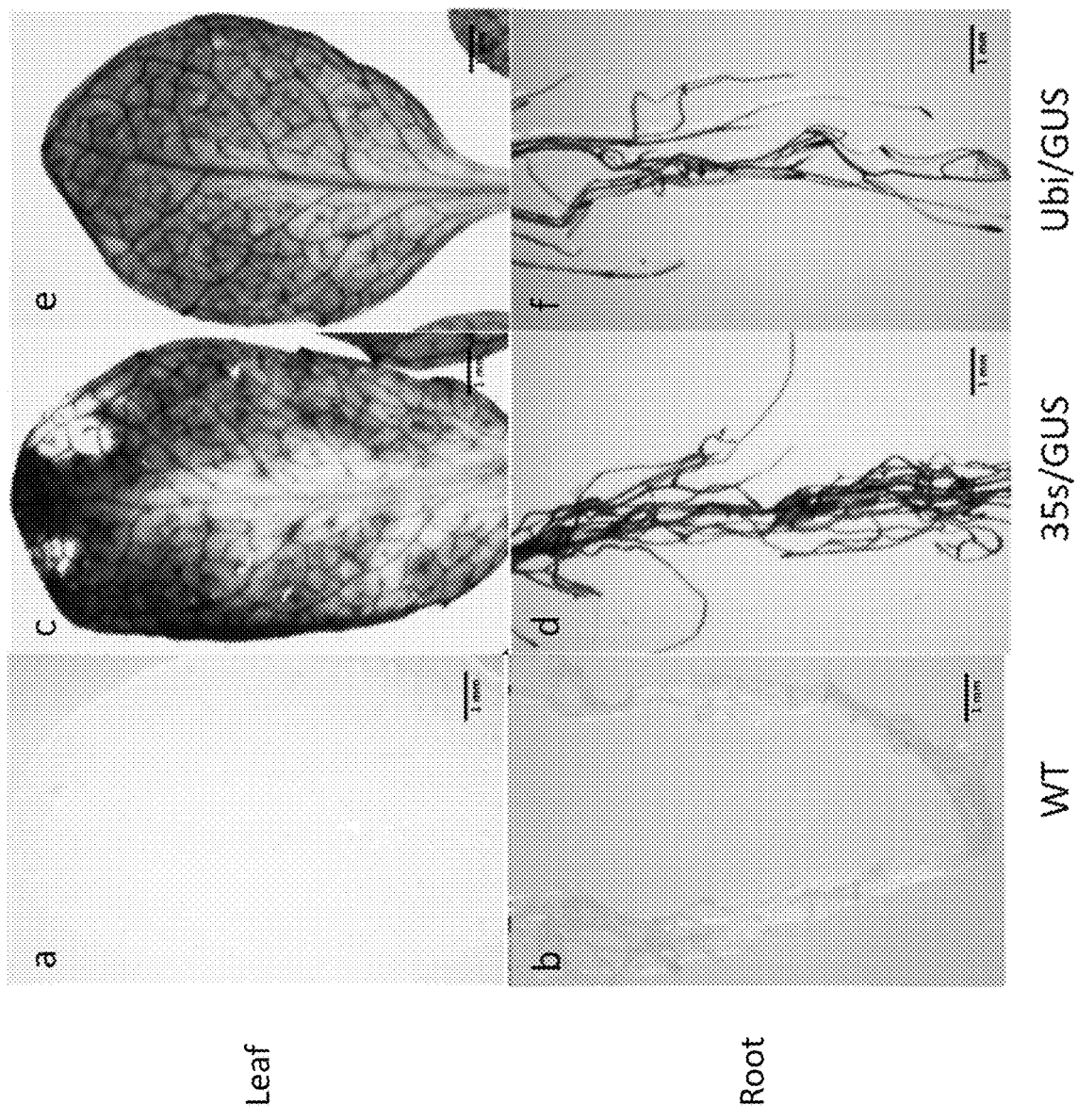
FIGS. 4A-4B show histochemical GUS-staining of two weeks old transgenic plants harboring different constructs.
Figure 4B:
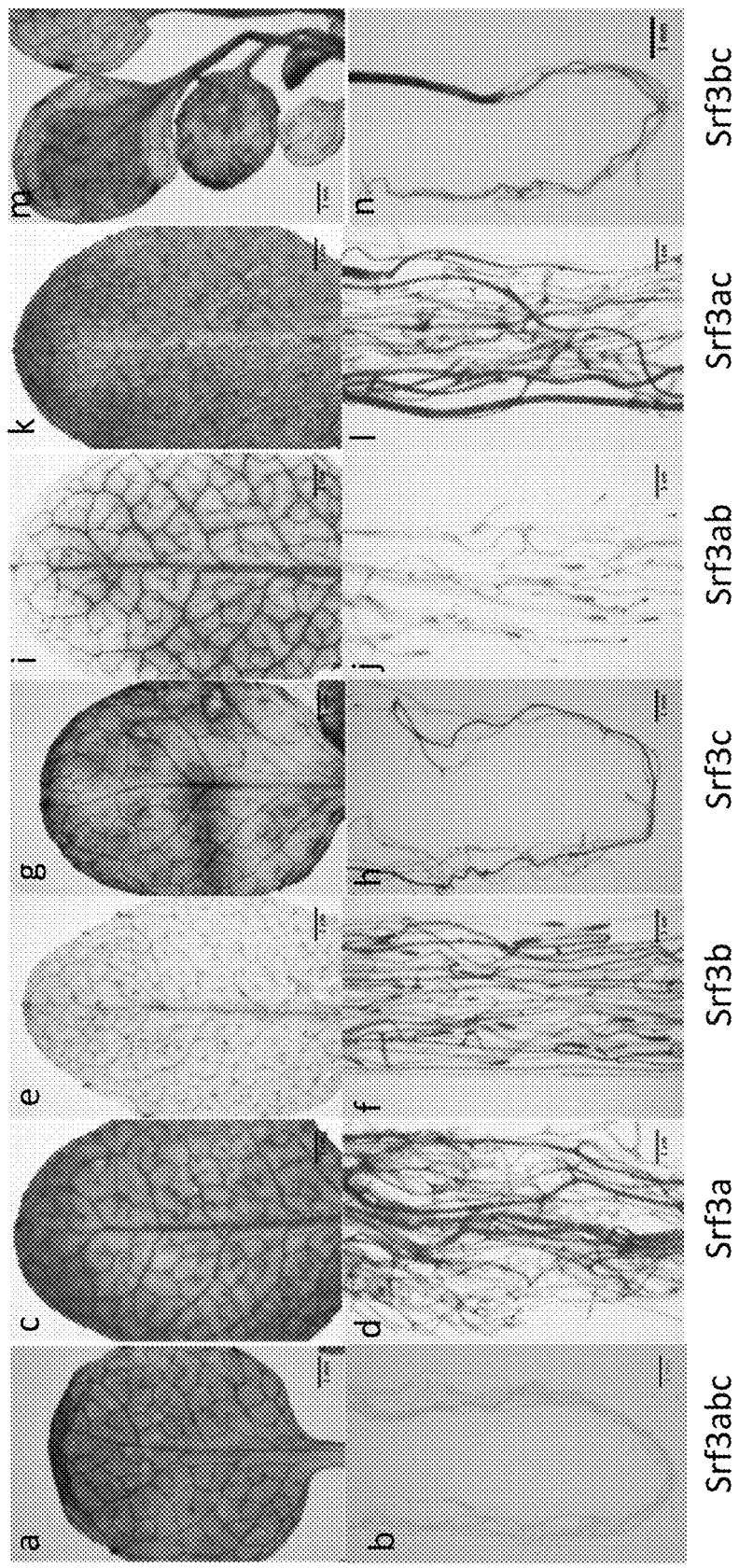

In two week old *Arabidopsis* seedlings, GUS activity (blue stain) was observed in both leaf tissue and root tissue in transgenic *Arabidopsis* plants harboring 35S/GUS or ubiquitin/GUS constructs (FIG. 4A, Panels c, d, e and f). In contrast to these two constitutive promoters, GUS activity was strongly detected in leaf tissue but not observed in root tissue in Sif3abc/GUS transgenic plants (FIG. 4B, Panels a and b). In the two deletion constructs (Sif3bc/GUS and Sif3c/GUS), the detection of blue stain in root tissues indicated that the tissue specific activity of the Sif3 promoter is altered by deleting the 5' end sequence, which may contain important cis-regions needed for leaf specific expression (FIG. 4B, Panels m, n, g, and h).

Figure 5A:
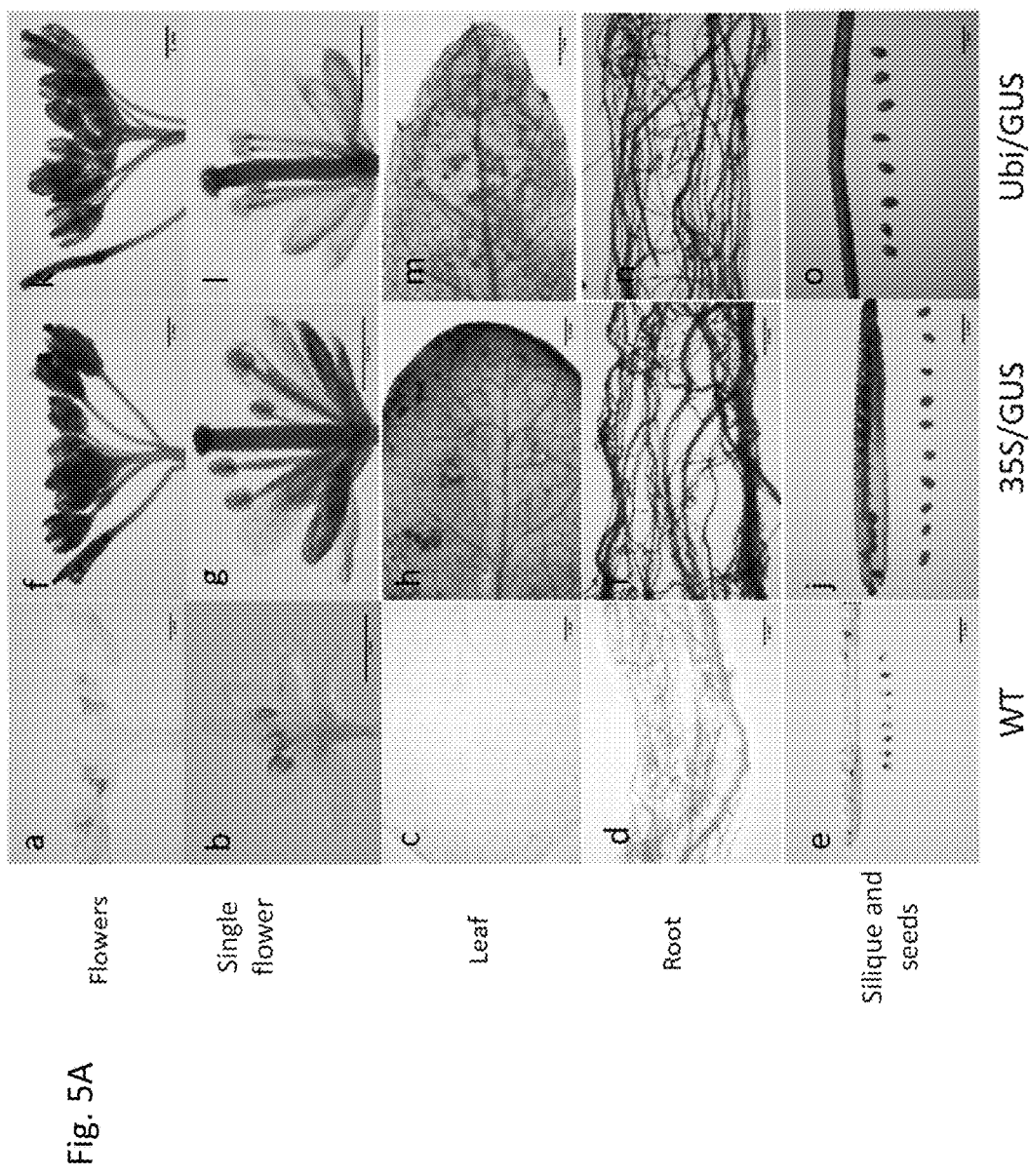
FIGS. 5A-5B show histochemical GUS-staining of four weeks old transgenic plants harboring different constructs.
Figure 5B:
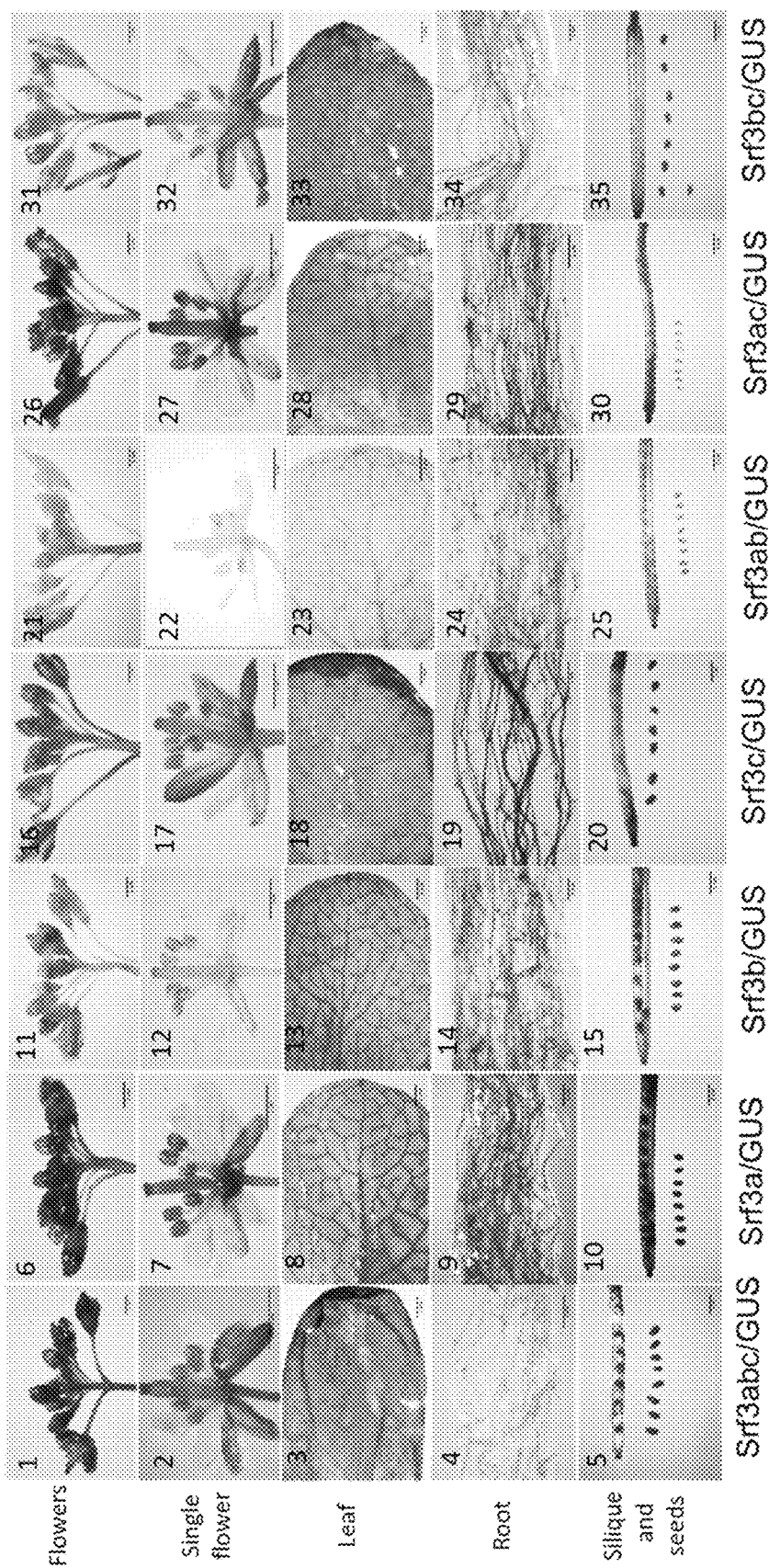

A similar result was observed in four week old flowering plants (FIG. 5A-B). In transgenic *Arabidopsis* plants harboring 35S/GUS construct, GUS activity was apparent in root, leaf, silique, and the whole floral organ including sepals, petals, filaments, anthers and stigmas (FIG. 5A, Panels f-j). Gus activity was observed in the ubiquitin/GUS transgenic plants in most of the tissues except anther and silique (FIG. 5A, Panels k-o). In the three Sif3/GUS transgenic lines, GUS activity was also strong but more tissue specific. In Sif3abc/GUS transgenic *Arabidopsis*, blue staining (i.e., GUS activity) was observed in leaf tissue and sepals, with only slight blue staining observed in root tissue (FIG. 5B, Panels 1-5). In Sif33bc/GUS and Sif3c/GUS transgenic *Arabidopsis*, strong blue stain was detected in leaves, sepals, siliques or pods (but not in the seeds) and root (FIG. 5B, Panels 31-35 and 15-20).

Thus, FIG. 5B shows that the full-length Sif3 promoter (Sif3abc) drives GUS gene expression in almost all parts except in roots, anthers, siliques, seed pods, and seeds (FIG. 5B, first column, panels 1-5). When the full-length promoter was broken into three fragments, Sif3a. Sif3b and Sif3c, and used to drive GUS gene, respectively, Sif3a and Sif3c can both drive high level of constitutive GUS expression (FIG. 5B, second and fourth columns, panels 6-10 and 16-20), and when combined together, Sif3ac also shows promoter activity, driving high level of constitute gene expression (FIG. 5B, sixth column, panels 26-30). However, Sif3b alone only shows very low promoter activity, and can barely drive gene expression in roots (FIG. 511, third column, panels 11-15). When Sif3a is fused to Sif3b to form Sif3ab, it shows promoter activity, but at a much lower level and no activity was observed in roots (FIG. 5B, fifth column, panels 21-25). When fusing Sif3b to Sif3c, the resulting Sif3bc also shows promoter activity to drive GUS expression, but the gene expression level in roots is much lower than that driven by Sif3c alone (FIG. 5B, last column, panels 31-35). These results suggest that the fragment Sif3b and portion of the 3' Sif3a may contain a regulatory element that determines tissue specificity, that is, the presence of this element prevents gene expression in roots. The possible sequences of this functional regulatory element are provides as SEQ ID NOs. 18-37.

Figure 6A:
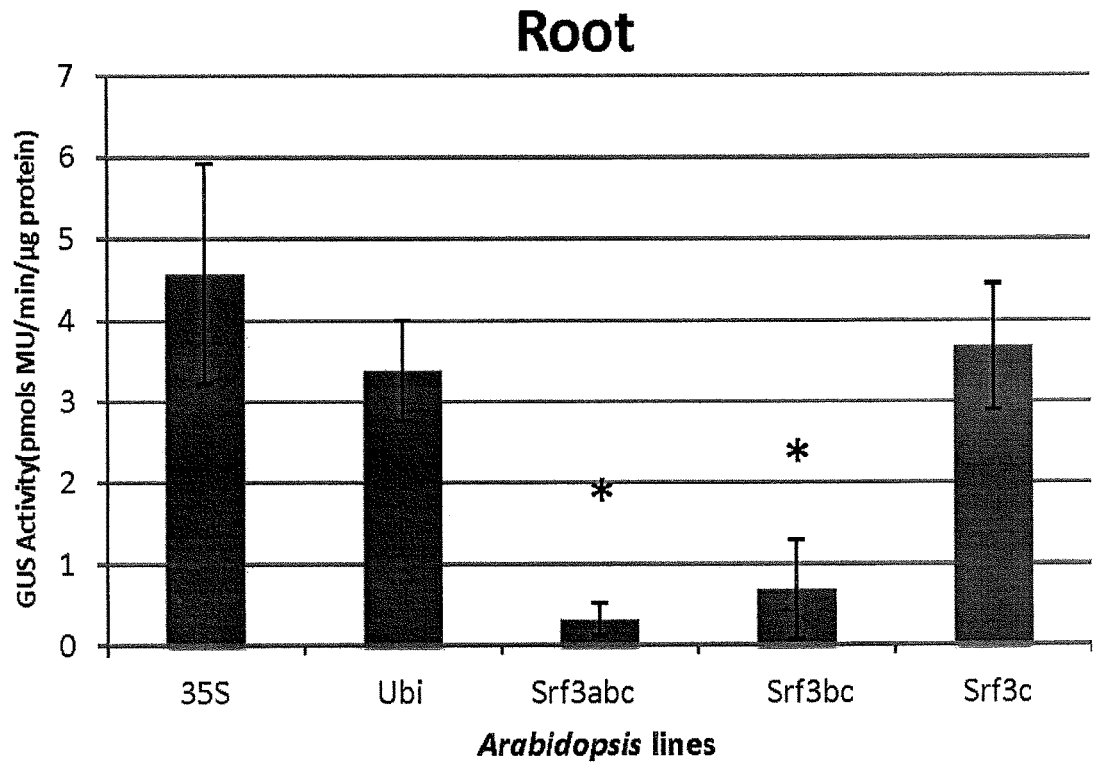
FIGS. 6A-6D shows Gus activity in different promoters in *Arabidopsis*.
Figure 6B:
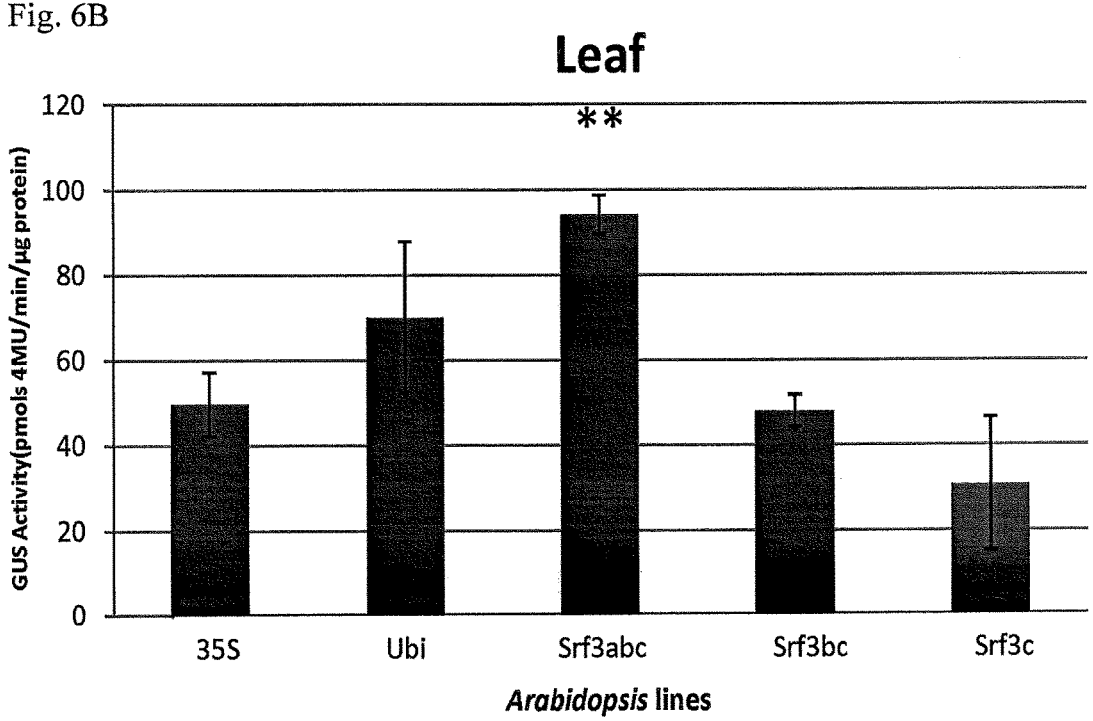
Figure 6C:
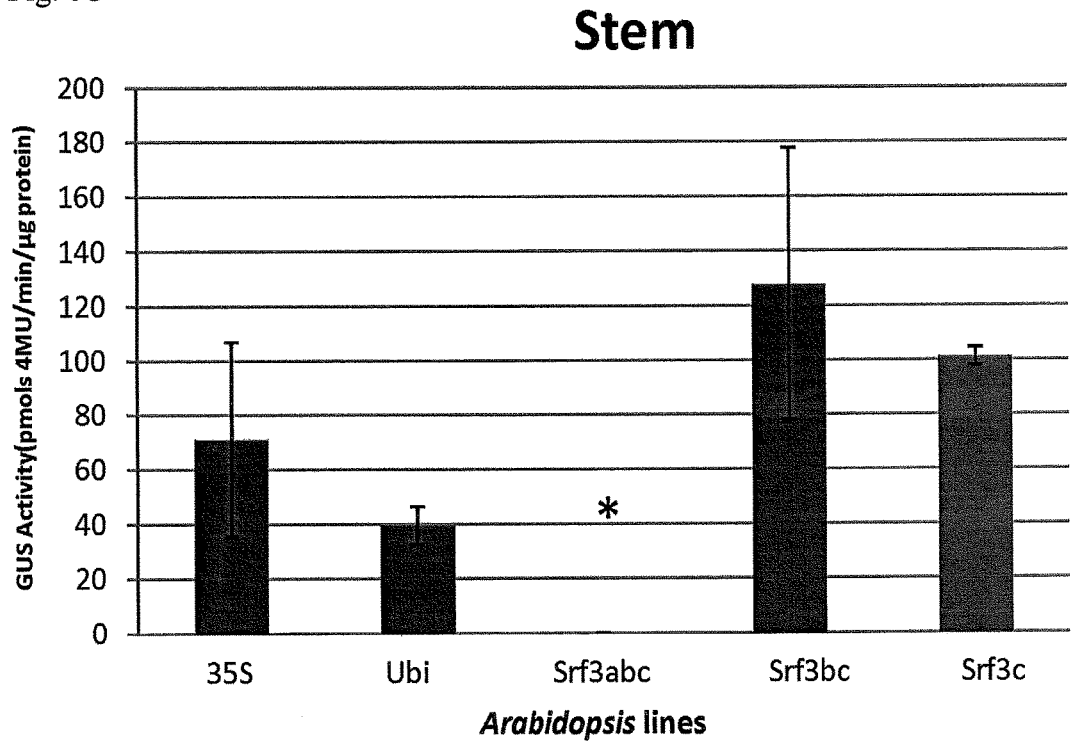
Figure 6D:
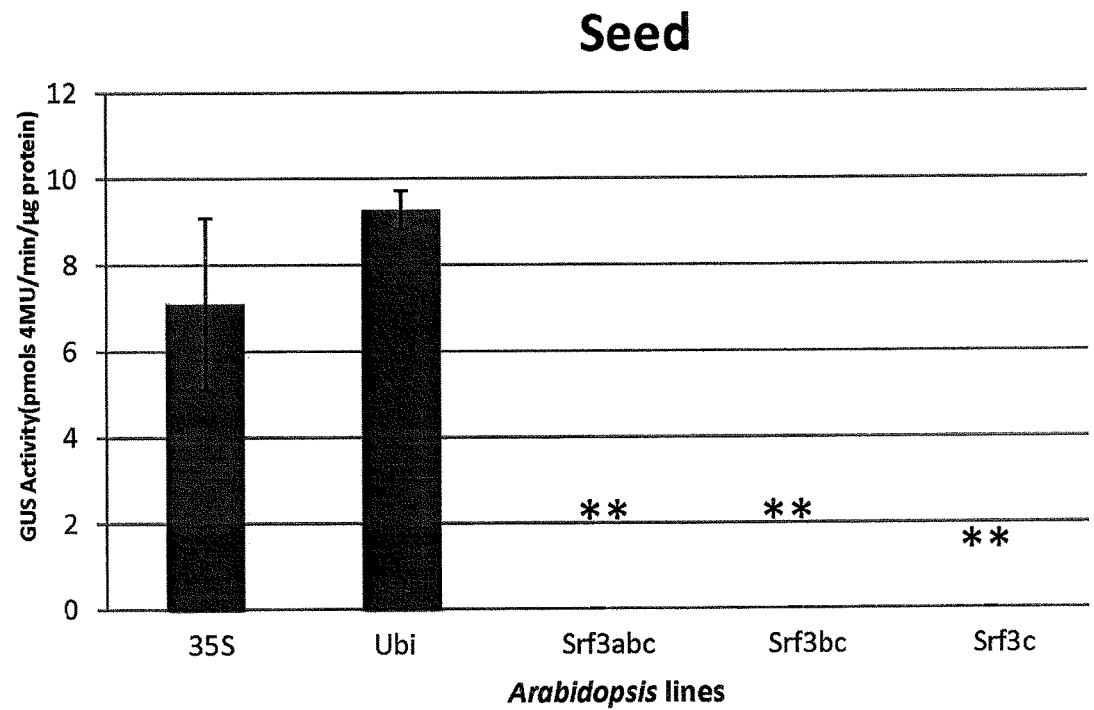

A GUS activity assay was conducted to measure the GUS activity in four-weeks old transgenic *Arabidopsis* quantitatively. As shown in FIG. 6, all three Sif3 promoters exhibited strong activity in *Arabidopsis* leaf tissue, with Sif3abc being the strongest promoter (FIG. 6B). Sif3a has an activity in the leaves of 200% or 134% when compared with the CaMV 35S promoter or the maize ubiquitin promoter, respectively, while Sif3bc and Sif3c have similar or slightly lower activities compared with the two constitutive promoters (FIG. 6B). In transgenic *Arabidopsis* root, the Sif3c promoter exhibited similar activity when compared with CaMV 35S and maize ubiquitin promoters, while Sif3a and Sif3bc promoter exhibited little or no activity in root tissue (FIG. 6A). In the transgenic *Arabidopsis* stem tissue, the Sif3bc and Sif3c promoters exhibited stronger activities when compared with CaMV 35s and maize ubiquitin promoters. The Sif33abc promoter exhibited no activity in root or stem tissue (FIG. 5B and FIG. 6C). Notably, none of the Sif3 promoters exhibited activity *Arabidopsis* seeds (FIG. 6D). The results were consistent with the histochemical GUS-staining results, indicating that the Sif3 promoter confers expression predominantly in leaf tissue and also indicating that deletion of Sif3abc 5' end modifies its tissue specificity.

Example 4. Characterization of the Srf3a Promoter Activity

Strongly constitutive promoters like CaMV 35s promoter are usually used to drive nucleic acid encoding a selectable marker in a transgenic plant because the high expression level of selectable markers could avoid the generation of false positive transgenic plants during the transformation process. Though there is no evidence to indicate that accumulation of proteins encoded by selectable marker genes like phosphinothricin acetyl transferase (PAT) or hygromycin phosphotransferase II (HPTII) or selectable markers themselves in edible parts of transgenic organisms used as human food or animal feed bring any harmful consequence (Herouet et al., *Regulatory Toxicology and Pharmacology* 41(2): 134-149 (2005)): Fuchs, R. L., et al. *Bio-Technology* 11(13):1543-1547 (1993)), the public still expresses concern about the safety of antibiotic/PPT resistance markers. A few methods have been developed to generate marker-free transgenic organisms (Komari et al. *Plant J.* 10(1):165-74 (1996); Jia et al. *Transgenic Research* 15(3):375-384 (2006); Mizutani et al. *Applied and Environmental Microbiology* 78(12):4126-4133 (2012)) including co-transformation and recombinase-mediated excision to delete the nucleic acids encoding the selection markers. However, these methods require a more complicated breeding process, and the deletion of nucleic acids encoding selection markers can be time-consuming and is inefficient. A more convenient method may be the adoption of green plant tissue specific promoters, which could promote the expression of selection markers in the leaf or stem only, thereby eliminating or reducing the accumulation of selection marker proteins and nucleic acids in fruit, seed or other edible tissues. Because of its leaf specific activity, Sif3 may be a good candidate for such as use as promoter.

Figure 7A:
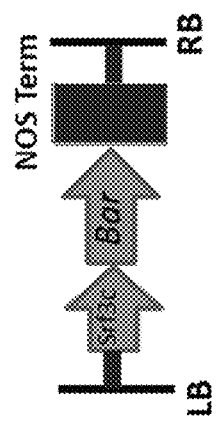
FIGS. 7A-7B.
Figure 7B:
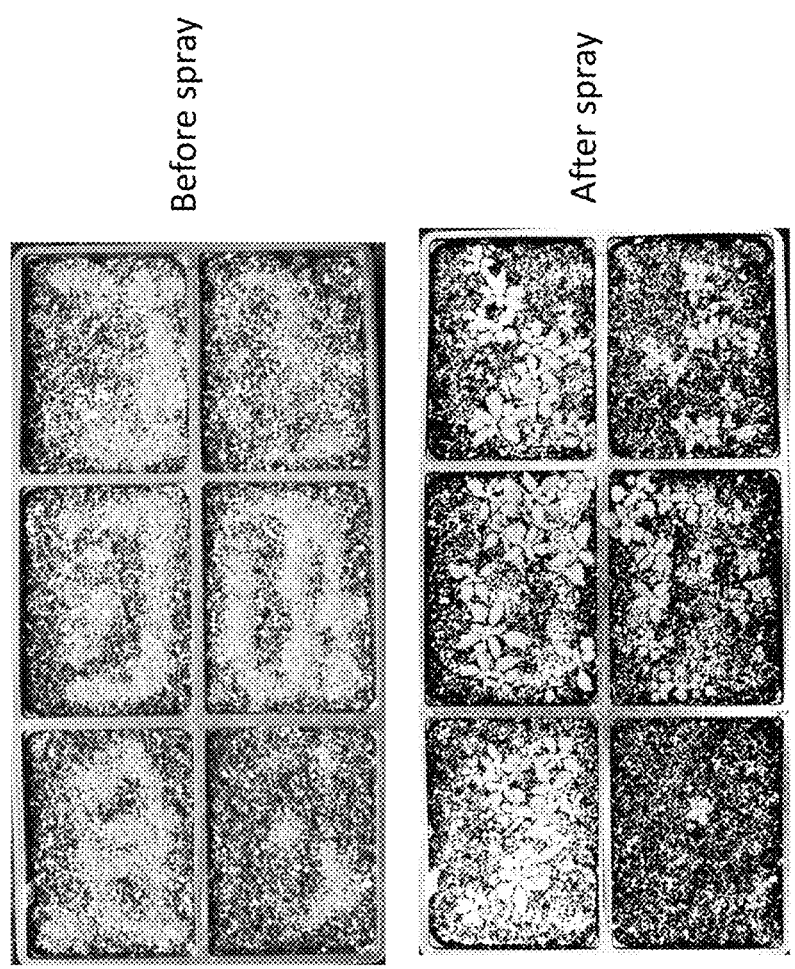

A construct was made in which Sif3c was operably linked to a nucleotide sequence encoding Bar, a broadly used herbicide resistance marker gene (FIG. 7A). Sif33c with a length of 400 bp length was used. The construct was transformed into *Agrobacterium tumefaciens* 4404, followed by transformation of *Arabidopsis* plants via the 'floral dip' method. Seeds were collected from the transformed *Arabidopsis* plants and sowed in soil. Two week old seedlings were sprayed with phosphinothricin (PPT). FIG. 7B shows that *Arabidopsis* harboring Sif3c/Bar/NOS expression cassette survived, indicating that Sif3c could be used as a leaf specific promoter to drive expression of nucleic acid sequences encoding selection markers.

Figure 10:
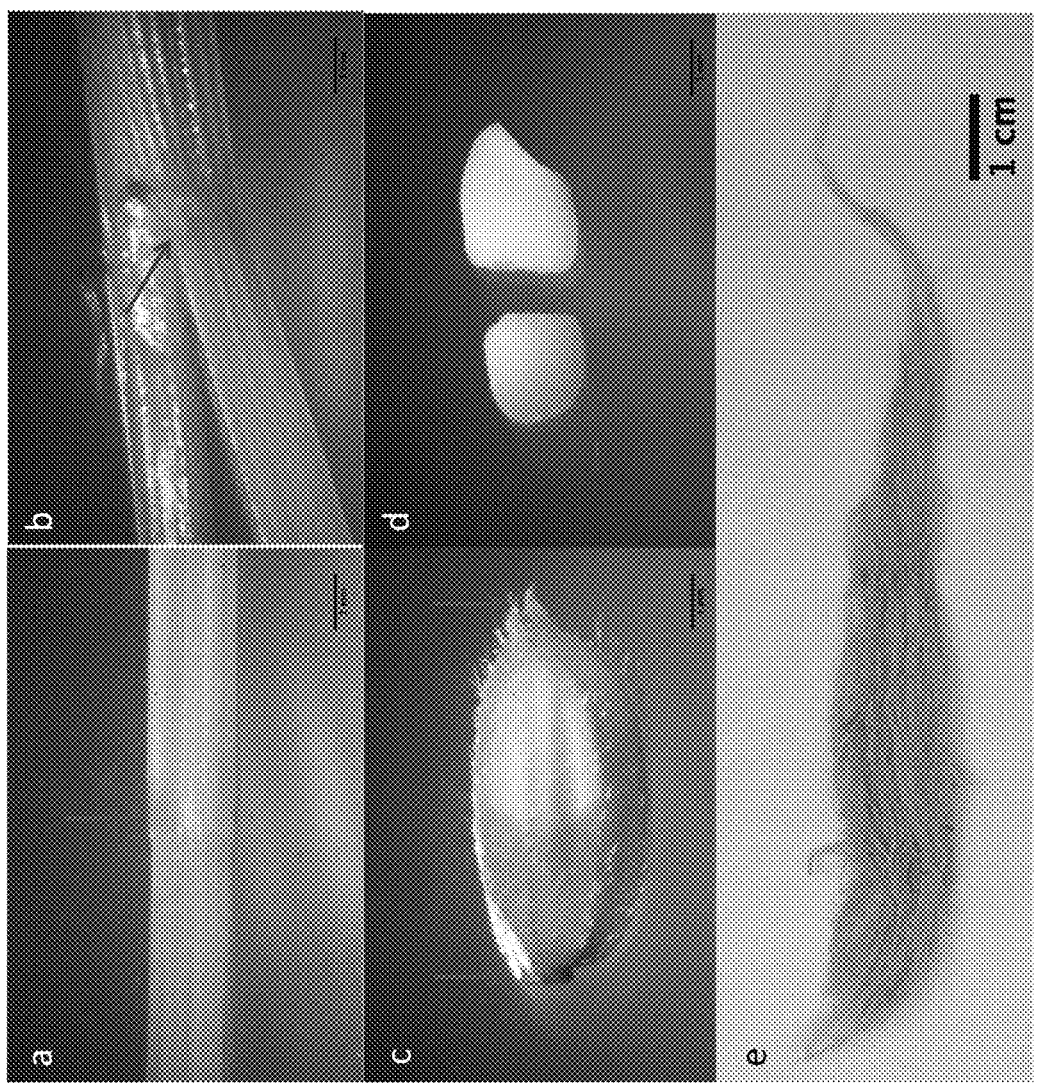
FIG. 10 shows GUS expression in *Oryza sativa* (rice) under control of the Sif3 promoter. Panels a and b show leaves. Panel c shows seed coat. Panel d shows seed. Panel e shows roots. Arrows point to the blue spots indicating expression of the GUS gene.

As a useful tissue specific promoter, Sif3 should not only have strong activity but also be functional in multiple species of plants. To determine whether Sif3 is functional in other species, we introduced Sif3abc/GUS construct into a dicot plant, tobacco (*Nicotiana tobacum*), and two monocot plants, including creeping bentgrass (*Agrostis stolonifera* L.) and rice (*Oryza sativa*). Base on the GUS staining result as shown in FIG. 8-FIG. 10, Sif3abc exhibits strong activity in tobacco, but weak activity in the two monocot plants. Because of the difficulty of performing the GUS staining assay in monocot plants, RT-PCR will be utilized to investigate the expression level of GUS gene in the two monocot plants.

Example 5. Further Characterization of the Srf3a Promoter Activity

Figure 3:
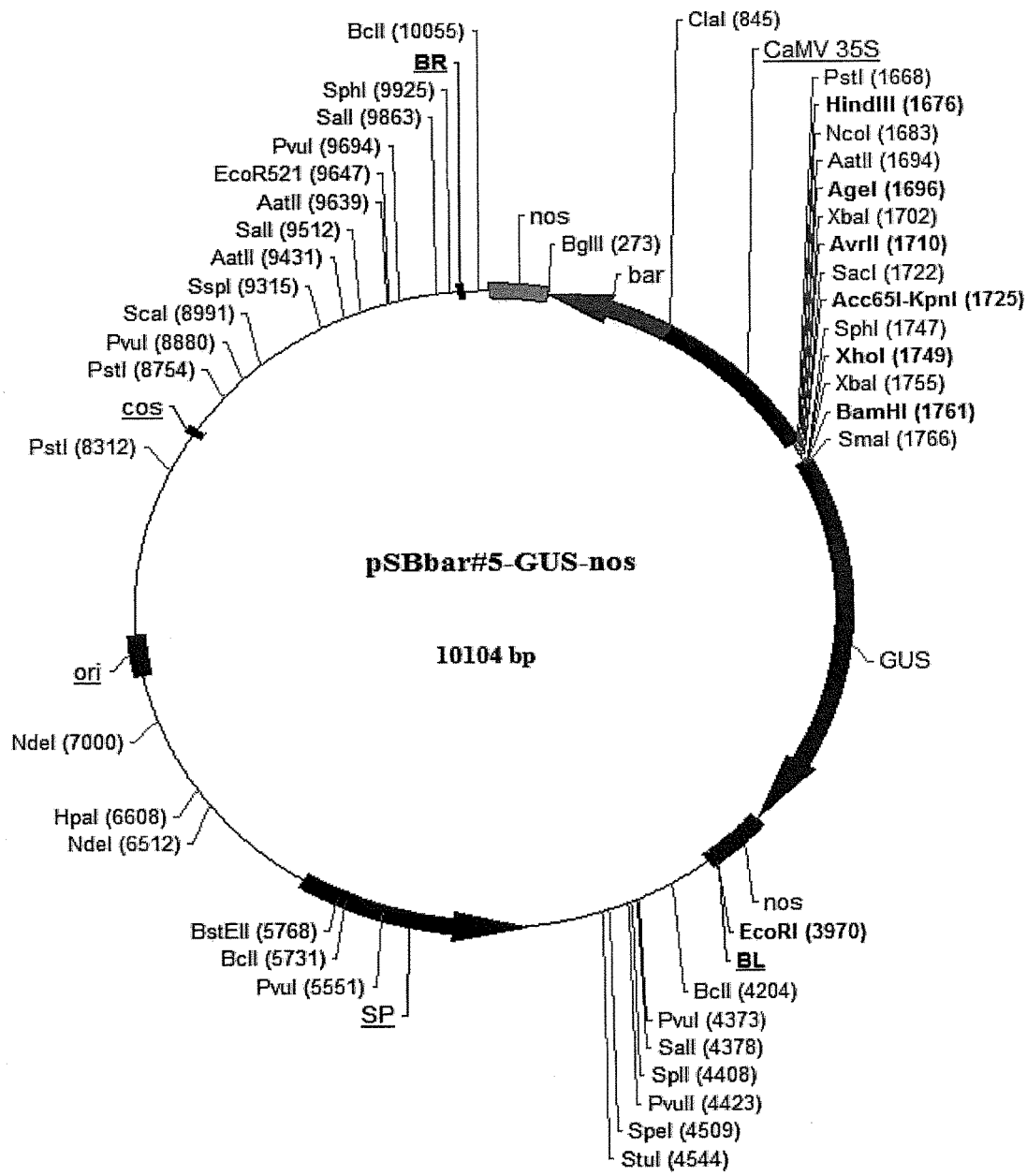
FIG. 3 shows schematic diagrams of pSBbar#5-GUS-nos vector.

To analyze the Sif3 promoter further and determine the region responsible for leaf specific activity, several constructs comprising various portions of the Sif3 promoter were generated as shown in FIG. 3. Thus, the Sif3abc construct comprises about 1524 bp of the Sif3 promoter operably linked to the GUS reporter gene. Sif3a comprises about 500 bp of the 5' portion, a, of the Sif3 promoter. Sif3b comprises about 638 bp from the middle portion, b, of the Sif3 promoter and Sif3c comprises about 383 bp of the 3' portion, c, of the Sif3 promoter. Sif3ab comprises about 1141 bp from the 5' end of the Sif3 promoter, a+b. Sif3ac comprises about 900 bp of the Sif3 promoter, from the 5' end and the 3' end, a+c and Sif3bc comprises about 1021 bp from the 3' end of the Sif3 promoter, b+c. As controls, constructs were generated comprising the CaMV 35S promoter and the ubiquitin promoter each operably linked to the GUS reporter gene. Plants were transformed with the constructs as described in Example 1, above.

Characterization of Transformed *Arabidopsis thaliana* Plants

*Arabidopsis* seedlings, two-weeks old (FIG. 4) and four weeks old (FIG. 5) transformed with a GUS reporter gene under control of a 35S promoter (CaMV 35S) or a ubiquitin promoter (Ubi) showed blue staining throughout the roots and leaves (FIG. 4) and flowers, roots, leaves (FIG. 5) as expected for constitutive promoters. Only plants transformed with the construct comprising the 35S promoter showed GUS expression in the siliques. No GUS expression was observed in the wild-type plants. FIG. 4 and FIG. 5 show two and four week old *Arabidopsis* seedlings, respectively, transformed with a GUS reporter gene under control of the entire Sif3 promoter (Sif3abc) or portions thereof. i.e., Sif3a, Sif3b, Sif3c, Sif3ab, Sif3ac, or Sif3bc.

GUS activity (pmols MU/min/µg protein) for the five different transgenic *Arabidopsis* lines harboring constructs in which GUS is operably linked to 35S, Ubi, Sif3abc, Sif3bc and Sif3c is shown in FIGS. 6A-6D. For each *Arabidopsis* line, plant samples were harvested from pooled plant tissues taken from at least 7 independent events. GUS activity was measured in root (FIG. 6A), leaf (FIG. 6B), stem (FIG. 6C) and seed (FIG. 6D).

Characterization of the Srf3 Promoter in Tobacco Plants, Creeping Bentgrass and Rice GUS expression under control of the Sif3 promoter was characterized in tobacco, creeping bentgrass, and rice. FIG. 8 show that the Sif3abc/GUS construct results in leaf specific expression in tobacco. The results show that sif3abc is only active in leaf tissue of tobacco, in despite of the age of the plants. FIG. 9 shows leaf specific GUS expression in *Agrostis stolonifera* (creeping bentgrass) using the Sif3abc promoter. FIG. 10 shows GUS expression in *Oryza sativa* (rice). The FIG. 9 and FIG. 10 indicate that the sif3abc promoter has weak activity in monocot plants.

The foregoing is illustrative of the present invention, and is not to be construed as limiting thereof. The invention is defined by the claims provided herein, with equivalents of the claims to be included therein.

All publications, patent applications, patents, patent publications, sequences identified by GenBank® Database accession numbers and/or SNP accession numbers, and other references cited herein are incorporated by reference in their entireties for the teachings relevant to the sentence and/or paragraph in which the reference is presented.

What is claimed is:

1. A recombinant nucleic acid molecule comprising
the nucleotide sequence of any one of SEQ ID NOs:1-3, or SEQ ID NOs:14-17, or any combination thereof,
wherein the nucleotide sequence is operably linked to at least one heterologous polynucleotide of interest to be transcribed.

2. An expression cassette comprising the recombinant nucleic acid molecule of claim 1 and (a) at least one regulatory sequence selected from an enhancer, an intron, a translation leader sequence, a transcription termination signal, a translation termination signal and a polyadenylation signal sequence, and/or (b) a selectable marker.

3. A cell comprising the recombinant nucleic acid molecule of claim 1, wherein the cell is a bacterial cell or a plant cell.

4. A plant or plant part comprising the recombinant nucleic acid molecule of claim 1.

5. A method of producing a plant and/or a plant part expressing at least one heterologous polynucleotide of interest, the method comprising:
introducing into a plant and/or plant part the recombinant nucleic acid molecule of claim 1, thereby producing a plant expressing the at least one heterologous polynucleotide of interest in the plant and/or plant part.

6. The method of claim 5, wherein the at least one heterologous polynucleotide of interest in the plant and/or plant part is expressed in a tissue-specific manner.

7. The method of claim 6, wherein the at least one heterologous polynucleotide of interest in the plant and/or plant part is expressed in most tissues but not in the roots, anthers, siliques, seed pods, or seeds.

8. The method of claim 5, wherein the plant part into which the recombinant nucleic acid molecule is introduced is regenerated into a plant comprising the recombinant nucleic acid and expressing the heterologous polynucleotide of interest.

9. A plant or plant part produced according to the method of claim 5.

10. A seed from the plant of claim 4, wherein said seed comprises in its genome the recombinant nucleic acid molecule.

11. A crop comprising a plurality of plants of claim 4, planted together in an agricultural field, a golf course, a residential lawn, an ornamental garden, a road side, an athletic field, and/or a recreational field.

12. A crop comprising a plurality of plants of claim 9, planted together in an agricultural field, a golf course, a residential lawn, an ornamental garden, a road side, an athletic field, and/or a recreational field.

13. A product produced from the plant or plant part of claim 4, wherein the product comprises a recombinant nucleic acid molecule comprising the nucleotide sequence of any one of SEQ ID NOs:1-3, or SEQ ID NOs:14-17, or any combination thereof, wherein the nucleotide sequence is operably linked to at least one heterologous polynucleotide of interest to be transcribed.

14. A product produced from the crop of claim 11, wherein the product comprises a recombinant nucleic acid molecule comprising the nucleotide sequence of any one of SEQ ID NOs:1-3, or SEQ ID NOs:14-17, or any combination thereof, wherein the nucleotide sequence is operably linked to at least one heterologous polynucleotide of interest to be transcribed.

15. A product from the plant or plant part of claim 9, wherein the product comprises a recombinant nucleic acid molecule comprising the nucleotide sequence of any one of SEQ ID NOs:1-3, or SEQ ID NOs:14-17, or any combination thereof, wherein the nucleotide sequence is operably linked to at least one heterologous polynucleotide of interest to be transcribed.

16. A processed product produced from the product of claim 13, wherein the harvested product comprises the recombinant nucleic acid molecule.

17. A product produced from the crop of claim 12, wherein the product comprises a recombinant nucleic acid molecule comprising the nucleotide sequence of any one of SEQ ID NOs:1-3, or SEQ ID NOs:14-17, or any combination thereof, wherein the nucleotide sequence is operably linked to at least one heterologous polynucleotide of interest to be transcribed.

18. A processed product produced from the product of claim 13, wherein the processed product comprises the recombinant nucleic acid molecule.

19. A processed product produced from the product of claim 15, wherein the processed product comprises the recombinant nucleic acid molecule.

20. A processed product produced from the product of claim 17, wherein the processed product comprises the recombinant nucleic acid molecule.

* * * * *